United States Patent
Coyle

(10) Patent No.: US 7,207,948 B2
(45) Date of Patent: Apr. 24, 2007

(54) SYSTEMS AND METHODS FOR MONITORING COUGH

(75) Inventor: Michael Coyle, Cambridge, MA (US)

(73) Assignee: VivoMetrics, Inc., Ventura, CA (US)

( * ) Notice: Subject to any disclaimer, the term of this patent is extended or adjusted under 35 U.S.C. 154(b) by 93 days.

(21) Appl. No.: 11/165,956

(22) Filed: Jun. 24, 2005

(65) Prior Publication Data

US 2006/0074334 A1    Apr. 6, 2006

Related U.S. Application Data

(60) Provisional application No. 60/582,520, filed on Jun. 24, 2004.

(51) Int. Cl.
 *A61B 5/00* (2006.01)

(52) U.S. Cl. ........................ 600/538; 600/529
(58) Field of Classification Search ................ 600/529, 600/538
See application file for complete search history.

(56) References Cited

U.S. PATENT DOCUMENTS

| | | | |
|---|---|---|---|
| 6,261,238 B1 * | 7/2001 | Gavriely | 600/532 |
| 6,436,057 B1 * | 8/2002 | Goldsmith et al. | 600/586 |
| 6,881,192 B1 * | 4/2005 | Park | 600/529 |
| 7,104,962 B2 * | 9/2006 | Lomask et al. | 600/529 |
| 2004/0249299 A1 * | 12/2004 | Cobb | 600/529 |

* cited by examiner

*Primary Examiner*—Charles A. Marmor, II
*Assistant Examiner*—Karen E. Toth
(74) *Attorney, Agent, or Firm*—Winston & Strawn LLP

(57) ABSTRACT

The present invention provides systems and methods for monitoring subjects, especially during sleep. Respiratory and sound data are recorded and coughs arousal are recognized as joint events in both of these signals having selected characteristics. Further, cough-arousal events during sleep are recognized when a likely cough occurs in association with a recognized EEG arousal. Cough arousal events are combined into a cough arousal index that reflects disease severity and sleep disruption due to cough. The methods of this invention are computer-implemented and can be provided as a program product including a computer readable medium. Measurements and indices provided by this invention can be used to monitor and to treat respiratory diseases.

45 Claims, 14 Drawing Sheets

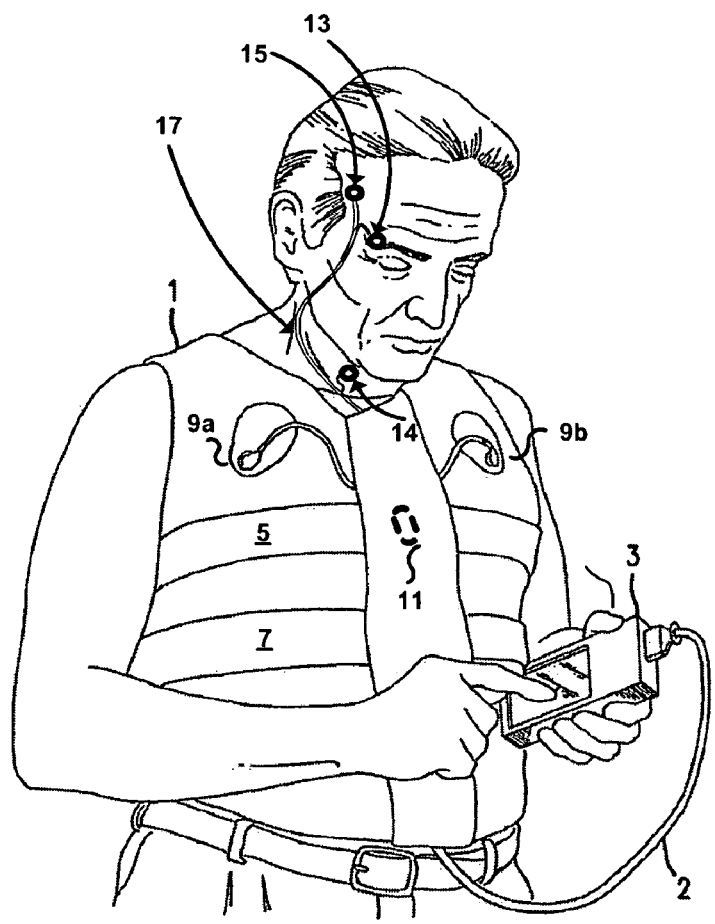
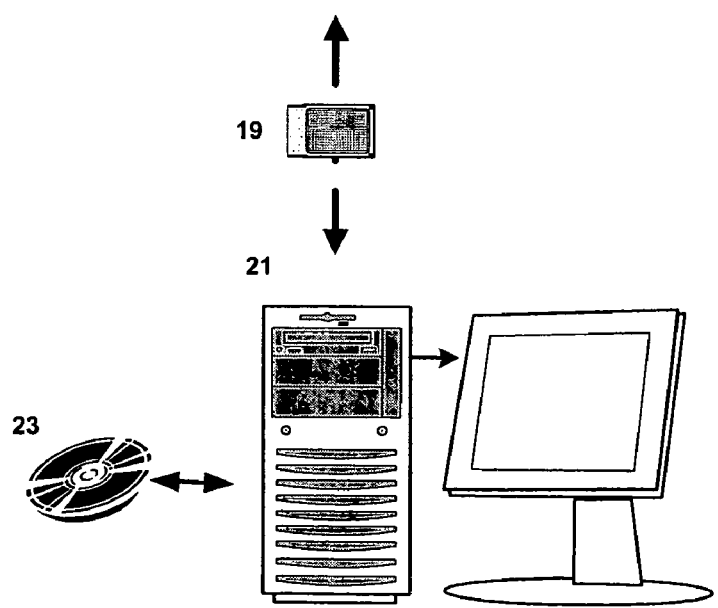
FIG. 1

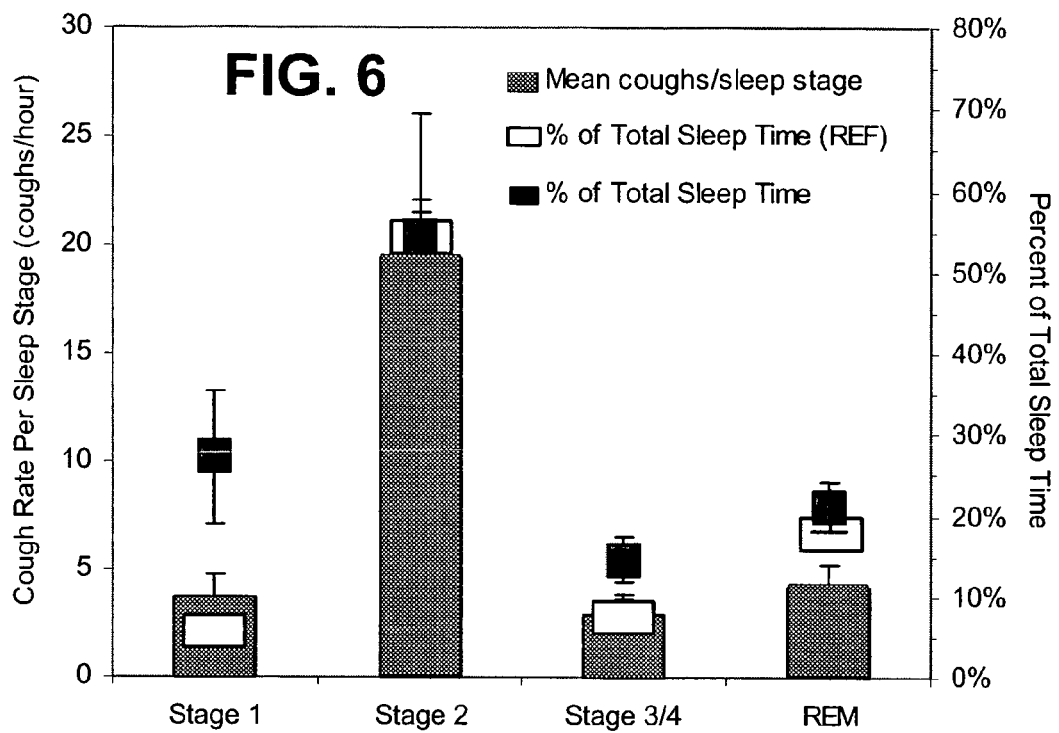
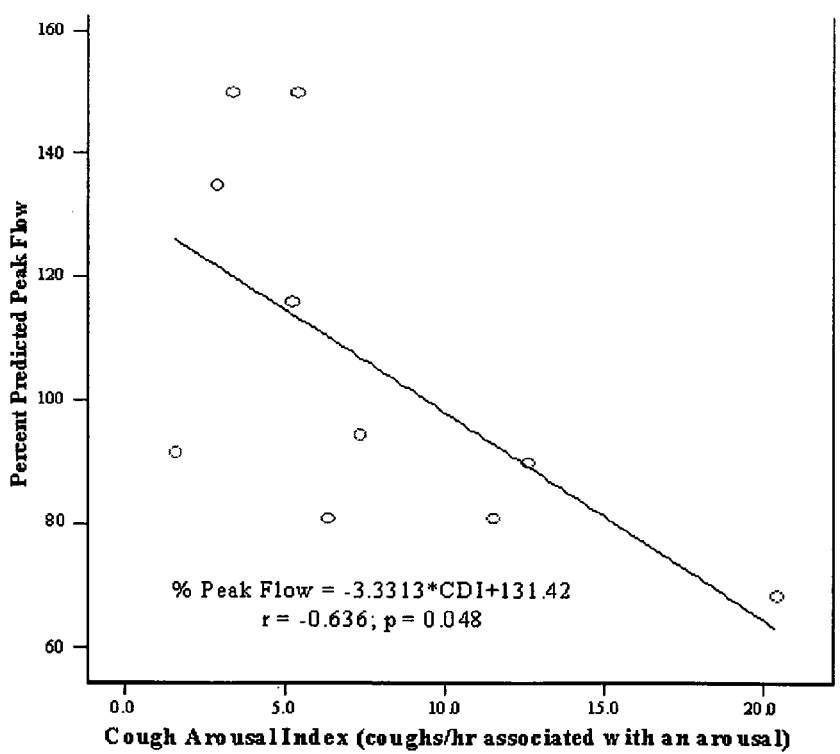
FIG. 7A

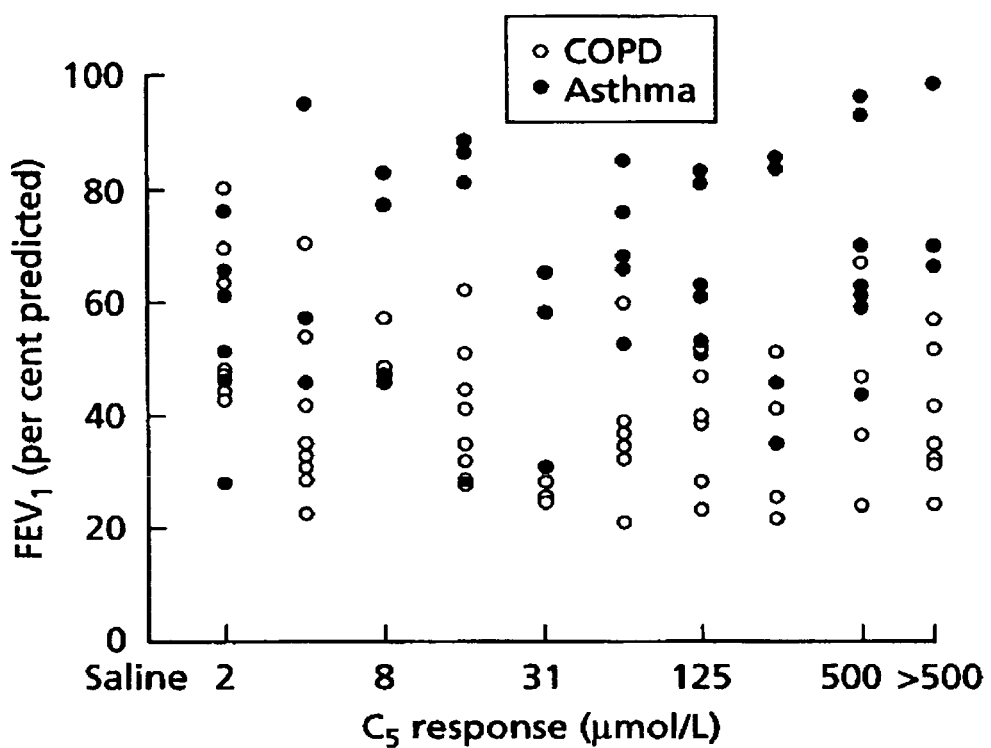
FIG. 7B
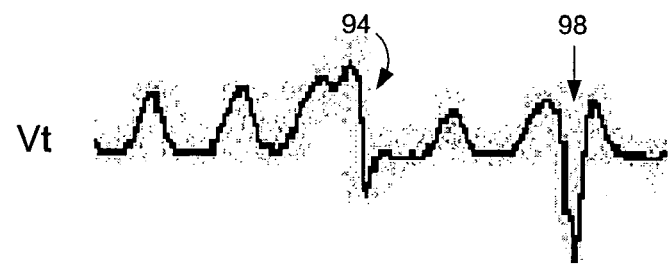
FIG. 8
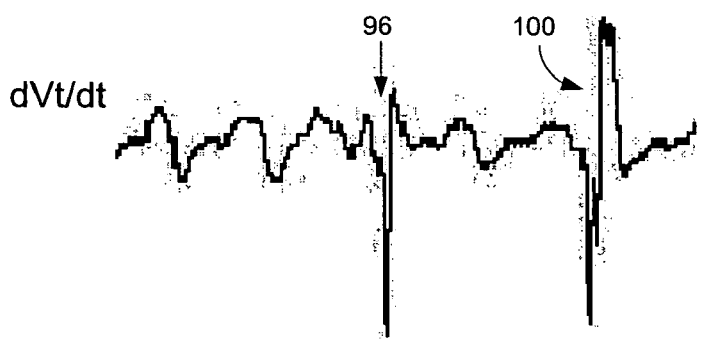

SYSTEMS AND METHODS FOR MONITORING COUGH

0. RELATED APPLICATIONS

This application claims benefit of and/or priority to U.S. provisional patent application Ser. No. 60/582,520, filed Jun. 24, 2004 and titled "SYSTEM AND METHOD FOR MONITORING COUGH DURING SLEEP" and to U.S. patent application Ser. No. 10/822,260, filed Apr. 9, 2004 and titled "SYSTEMS AND METHODS FOR RESPIRATORY EVENT DETECTION".

1. FIELD OF THE INVENTION

The present invention provides systems and methods for real-time physiological monitoring, particularly of a sleeping subject in a home environment, and more particularly of cough frequency and EEG arousals during sleep. The invention is also useful for monitoring awake and/or ambulatory subjects.

2. BACKGROUND OF THE INVENTION

Cough is a frequent complaint of COPD (chronic obstructive pulmonary disease) patients (and other patients) that can significantly impact quality of life at both a functional and a nuisance level. It is expected that understanding cough in disease progression and treatment will enable more targeted treatments and better understanding of the patient's disease experience. However, true cough frequency and its circadian distribution remain relatively unknown because it has been difficult to objectively quantify cough in the 'real world environment' for a number of technical reasons leaving. Objective quantification of cough by other routine has been difficult and time consuming for both researchers and subjects.

Moreover, the art lacks portable and easy-to-use monitoring methods and systems that provide objective and quantitative data on cough and, for cough during sleep, accompanying EEG arousals. In the inventor(s) experience, no portable device has heretofore demonstrated an ability to recognize coughs and to monitor cough frequency or to provide concurrent cough and EEG data. Although a number of portable devices for assessing daytime and night time cough have been reported, none has been reported to assess night time cough together with its influence on sleep architecture as revealed by electroencephalography (EEG). See, e.g., Cox et al., 1984, An electromyographic method of objectively assessing cough intensity and use of the method to assess effects of codeine on the dose-response curve to citric acid. *British Journal of Clinical Pharmacology* 18: 377–382, 1984; Munyard et al., 1994, A new device for ambulatory cough recording. *Pediatric Pulmonology* 18: 178–186, 1994; and Subburaj et al., 1996, Methods of recording and analyzing cough sounds. *Pulmonary Pharmacology* 9: 269–279, 1996.

Considerable confusion in the art has resulted from this lack of objective methods and systems for monitoring cough and sleep. On one hand, it has been previously reported that sleep suppresses cough. See, e.g., Hsu et al., Coughing frequency in patients with persistent cough: assessment using a 24 hour ambulatory recorder. *European Respiratory Journal* 7: 1246–1253, 1994. Studies from EEG laboratories have reported that cough is almost completely absent in stage 3 and 4 sleep (deep sleep) and is further not thought to be accompanied by night time awakenings. See, e.g., Power et al., 1984, Nocturnal cough in patients with chronic bronchitis and emphysema. *American Review of Respiratory Disease* 130: 999–1001, 1984. On the other hand, it has also been reported that the nocturnal cough and wheezing associated with asthma may impact sleep quality. In the study of Selby et al., 1997, Inhaled salmeterol or oral theophylline in nocturnal asthma? *American Journal of Respiratory & Critical Care Medicine* 155: 104–108, 1997, patients either received 50 μg salmeterol or individually dose-titrated sustained-release oral theophylline. Post salmeterol treatment, patients reported an improved quality of life. The authors did observe fewer nocturnal arousals, but they did not indicate whether the arousals were due to airway obstruction or to cough. Sleep architecture did not appear to differ pre/post treatment.

On the other hand, others report that sleep in patients with a number of sleep disorders, pulmonary disorders, and in some elderly is punctuated with frequent, brief arousals. The arousals are transient and generally do not result in behavioral awakening, reoccurring in some conditions as often as once per minute. The arousing stimulus differs in the various disorders and can be identified in some cases (i.e. cough, apnea, leg movements, pain), whereas in other cases (i.e. "normal" sleep of elderly, some insomnias) it is idiopathic. EEG data during sleep reveals patients arouse to cough. Thus, multiple cough bouts over the course of the night yield multiple arousals and, therefore, may ultimately influence over all sleep quality. The important fact is that the arousals result in fragmented sleep rather than shortened sleep. Just as with shortened sleep, it now is clear that sleep fragmentation leads to increased daytime sleepiness and other deleterious effects.

This lack of objective and quantitative cough and sleep monitoring methods and systems has thus led to confusion in the art and has hindered management of COPD, asthma, and similar conditions. Such methods and systems would therefore benefit medical research and medical practice.

A number of references are cited herein, the entire disclosures of which are incorporated herein, in their entirety, by reference for all purposes. Further, none of these references, regardless of how characterized above, is admitted as prior to the invention of the subject matter claimed herein.

3. SUMMARY OF THE INVENTION

The objects of this invention include objective and quantitative cough monitoring methods and systems in waking and sleeping subjects. Further methods and systems monitor sleep disturbance due to cough by also processing EEG data. This invention will aid in management of COPD (chronic obstructive pulmonary disease), asthma, and similar conditions (e.g., cystic fibrosis (CF)) and will also promote medical research.

The systems and methods of this invention monitor subjects and gather respiratory and electroencephalographic (EEG) data. This respiratory data is processed to, inter alia, objectively recognize cough occurrences. In controlled research environments, accuracies up to 99% have been verified by application of the methods of this invention to subjects also observed by simultaneous video recording. Similar accuracies are also achieved and evidenced in "real life" situations, both waking and sleeping. The EEG data is processed to, inter alia, recognize abrupt changes in frequency that reflect brief arousals (suggestive of an awake state) similar to those that can be manually identified on routine polysomnograms. If electromyographic (EMG) data is available in an embodiment, such arousals can be corroborated by brief increases in EMG amplitude. These arousals are brief and transient, and therefore can cause uncertainties reading the standard 20 or 30-second epoch sleep stage scoring system or be overlooked entirely. See, e.g., Bonnet et al., 1992, EEG arousals: scoring rules and examples—a preliminary report from the sleep disorders atlas task force of the American sleep disorders association, *Sleep* 15: 173–184, 1992.

The processed monitoring data is preferably then combined to determine new clinically relevant outcome variables, the cough arousal index (CAI) and a cough disturbance index (CDI). This CAI reflects the number of nocturnal coughs associated with an EEG arousal during each hour of sleep. If nocturnal coughs are not associated with an EEG arousal, they are counted in a cough disturbance index (CDI) which is defined by the number of coughs per hour of sleep not associated with an arousal. These new indices are for medical management of individual patients and also for medical research, for example, for the understanding of the anti-tussive and/or pro-tussive profiles of pharmacological compounds.

In more detail, the present invention provides methods for monitoring a subject during sleep by recording respiratory and EEG data, by recognizing the occurrences of coughs from the respiratory data, by recognizing the occurrences of transient EEG arousals from the EEG data; and by detecting and cough-arousal event when a recognized event occurs in association with a recognized EEG arousal. The methods further determine a cough arousal index as the number of cough-arousal events per time period during sleep. The present invention also provides systems for monitoring a subject during sleep that preferably include garments comprising sensor for respiratory and EEG signals, and a computer system in data communication with the garment for performing the methods of this invention. The present invention also provides a program product with a computer readable medium on which are encoded instructions for performing the methods of this invention. Further embodiments provides methods for use of a cough arousal index: for treating a patient subject to cough by determining the patient cough arousal index; and administering medication in order that the patient's cough arousal index is within selected bounds; and for evaluating a therapeutic agent by administering the therapeutic agent to a subject; and monitoring the subject's cough arousal index.

This invention includes the following embodiments. In a first embodiment, this invention includes a computer-implemented method for monitoring cough in a subject that processes tidal volume ($V_T$) data obtained from said subject in order to recognize a respiratory event when a peak-to-peak amplitude of a breath exceeds a threshold; processes sound data obtained from said subject in order to recognize a sound event when a sound envelope exceeds a threshold; processes each recognized event respiratory to determine if it temporally overlaps a sound event and further to determine if it has an expiration-inspiration pattern characteristic of a cough; and selects as a cough event each respiratory event that overlaps a sound event and that has said characteristic expiration-inspiration pattern.

Selected aspects of this embodiment include obtaining sound data from a sensor in contact with, or in close proximity to, said subject's throat; and further processing accelerometer data obtained from said subject in order to recognize motion of said subject; to retain said selected cough event if no subject motion is recognized during said cough; and otherwise to discard said cough event if subject motion is recognized during said cough.

In a second embodiment, this invention includes a computer-implemented method for monitoring cough in a subject that processes respiratory data and sound data obtained from said subject in order to recognize cough events; processes said EEG data obtained from said subject in order to recognize transient arousal events; and detects a cough-arousal (CA) event when a recognized cough event occurs in association with a recognized EEG arousal event.

Selected aspects of this embodiment include processing accelerometer data obtained from said subject in order to recognize motion of said subject; retain said selected cough event if no subject motion is recognized during said cough; and otherwise discard said cough event if subject motion is recognized during said cough; and further comprising determining a CA index (CAI) for a selected period of time as the number of CA events during said selected period of time and a plurality of CAIs for selected periods of time spanning a period of sleep of said subject.

In a third embodiment, this invention includes a computer-implemented method for monitoring cough in a subject that processes tidal volume ($V_T$) data and sound data in order to recognize coughs and further processes each cough event to determine a ratio of the depth of said cough event to a mean expiratory volume during a period of quiet breathing. Selected aspects of this embodiment then classify as a cough of cystic fibrosis if said ratio is in a range determined to be characteristic of cystic fibrosis coughs, or as a post-infectious cough if said ratio is in a range determined to be characteristic of post-infectious coughs, said post-infections range being less than said cystic fibrosis range; or as a cough of chronic obstructive pulmonary disease (COPD) if said ratio is in a range determined to be characteristic of COPD coughs, said COPD range being less than said post-infectious range.

In a fourth embodiment, this invention includes a system for monitoring a subject during sleep having a monitoring garment comprising sensors providing respiratory signals, sound signals, and EEG signals from said subject; and a computer system comprising a computer-readable memory comprising encoded instructions for receiving said sensor signals; processing said respiratory signals and said sound signals in order to recognize cough events; processing said EEG signals in order to recognize transient arousal events; detecting a cough-arousal (CA) event when a recognized cough event occurs in association with a recognized EEG arousal event; and determining a CA index (CAI) for a plurality of selected time periods as the number of CA events during said selected period of time.

Selected aspects of this embodiment include processing said accelerometer signals in order to recognize motion of said subject; retain said selected cough event if no subject motion is recognized during said cough; and otherwise discard said cough event if subject motion is recognized during said cough; and a sensor providing sound signals is in contact with, or in close proximity to, said subject's throat.

This inventions also includes program products comprising computer readable media on which are encoded instructions for practicing the methods of this invention in all their aspects. Further applications of this invention include methods directed to solving medical and pharmaceutical problems. For example, one such method is for treating cough in a subject that determines cough disturbance indices (CDI) for said subject for selected periods of time as the number of cough events during said selected periods of time, said cough events being determined by the method of claim 1;

and administers an anti-tussive therapeutic agent to said subject in order that said CDIs are within selected bounds.

Another such method is for treating disordered sleep in a subject due to cough during sleep that determines cough arousal indices (CAI) for selected periods when the subject is sleeping as the number of cough arousal events during said selected periods of time during sleep, said cough arousal events being determined by the method of claim 1; and administers an anti-tussive therapeutic agent to said subject in order that said CAIs are within selected bounds. A further such method is for evaluating a therapeutic agent in a subject that determines prior cough disturbance indices (CDI) for said subject for selected periods of time administers said therapeutic agent to said subject; determines subsequent CDIs for said subject for further selected periods of time; and compares said prior CDIs with said subsequent CDIs to determine an effect of said therapeutic agent on cough of said subject.

This inventions also includes further aspects of this methods and further embodiments that will be recognized from the following description, figures, and claims.

Specific embodiments of this invention will be appreciated from the following detailed descriptions and attached figures, and various of the described embodiments are recited in appended claims.

4. BRIEF DESCRIPTION OF THE DRAWINGS

The present invention may be understood more fully by reference to the following detailed description of preferred embodiments of the present invention, illustrative examples of specific embodiments of the invention, and the appended figures in which:

FIG. 1 illustrates a wearable monitoring device and associated processing system;

FIG. 6 illustrates an example of disturbed sleep architecture in subjects with COPD;

Figure 9:
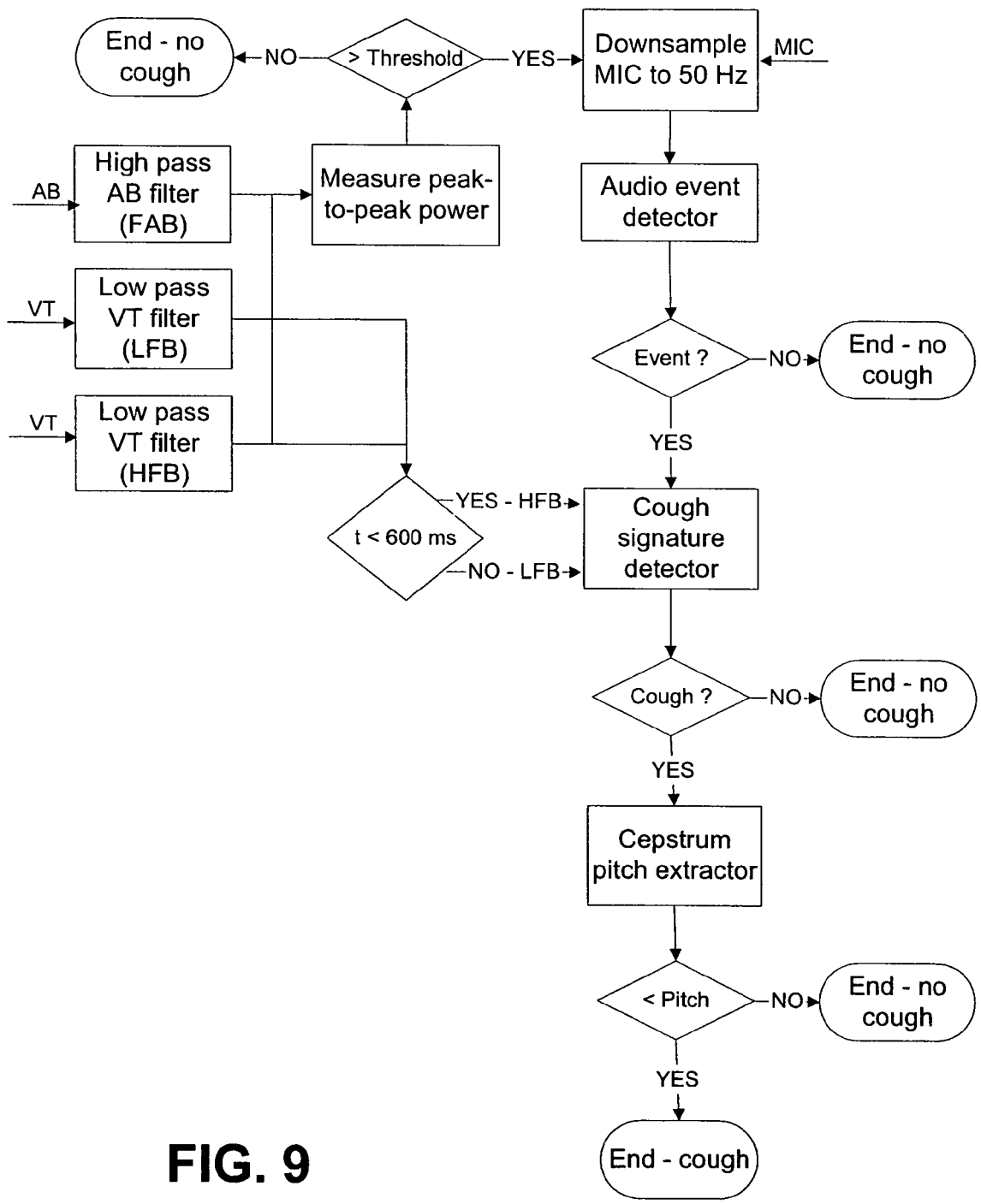
Figure 10A:
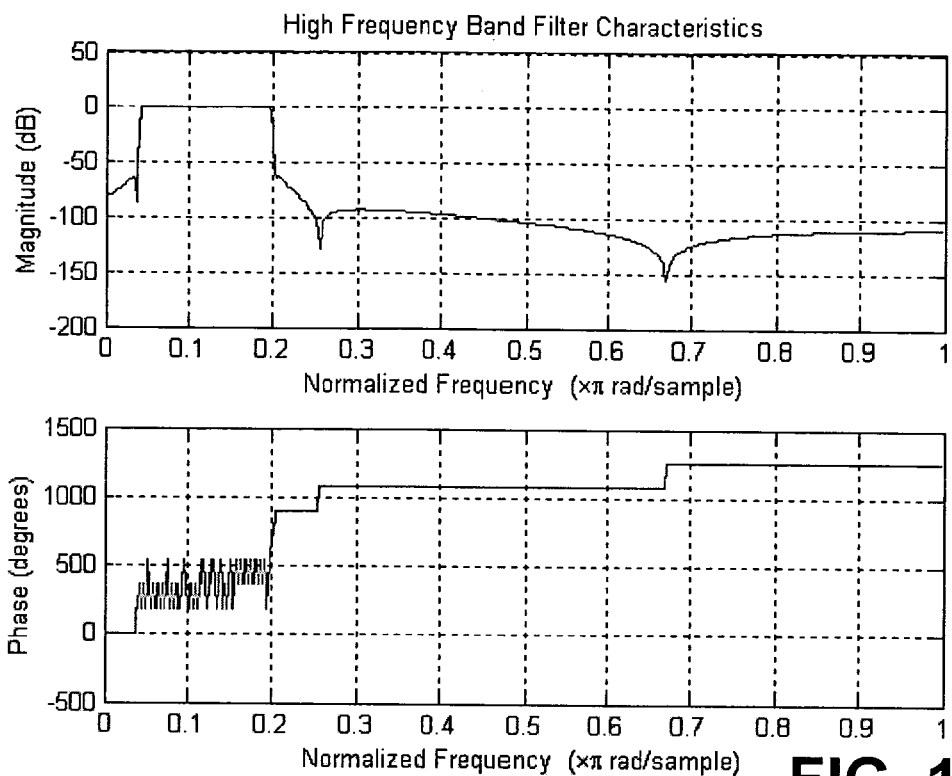
Figure 10B:
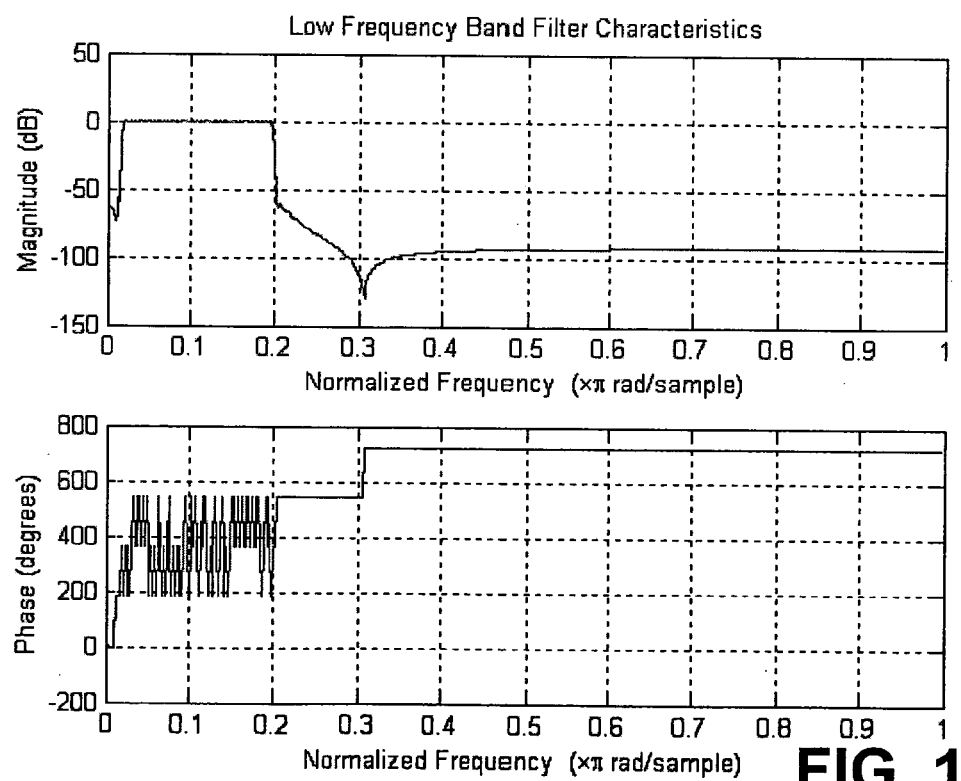
Figure 11:
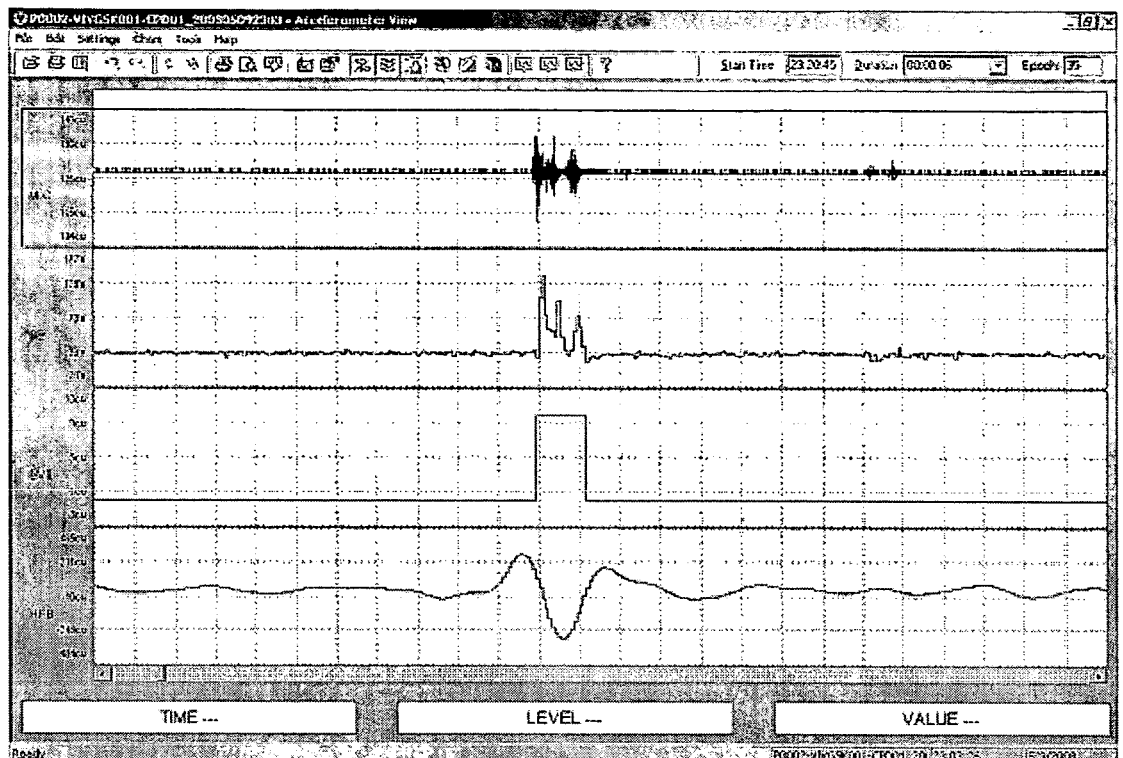
Figure 12:
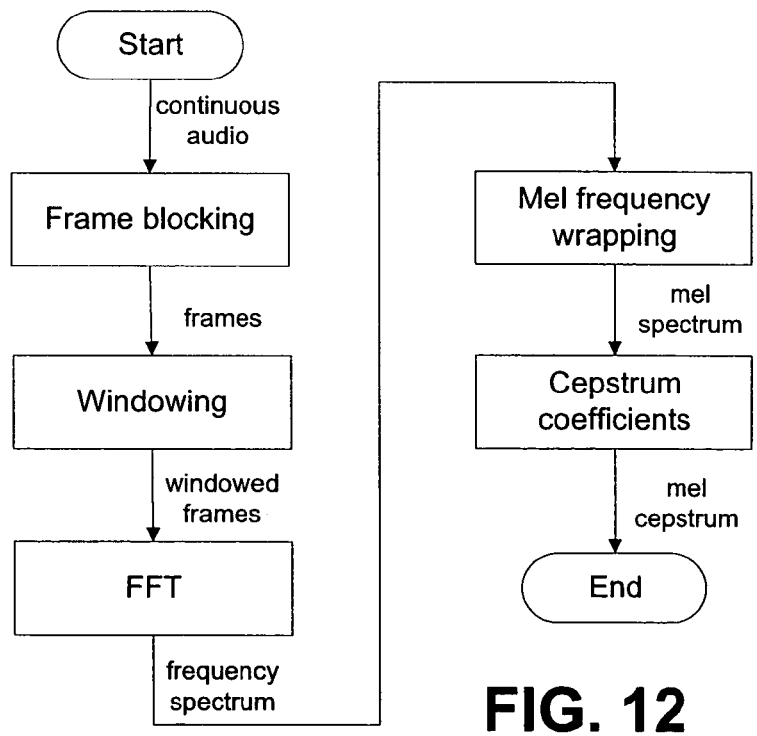
Figure 14A:
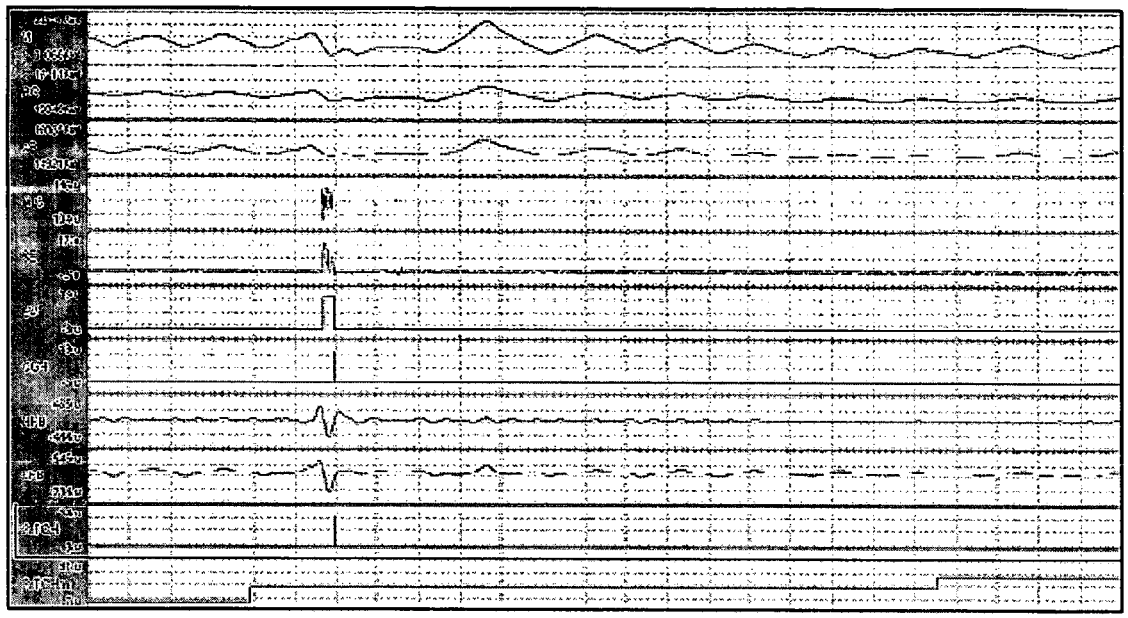
Figure 14B:
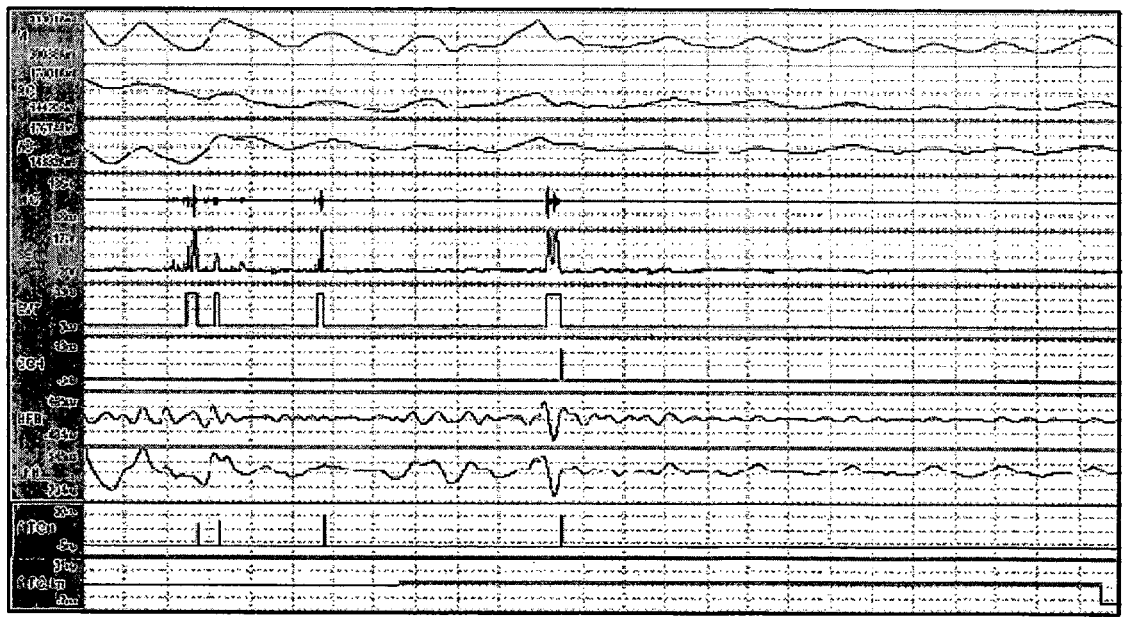
Figure 15A:
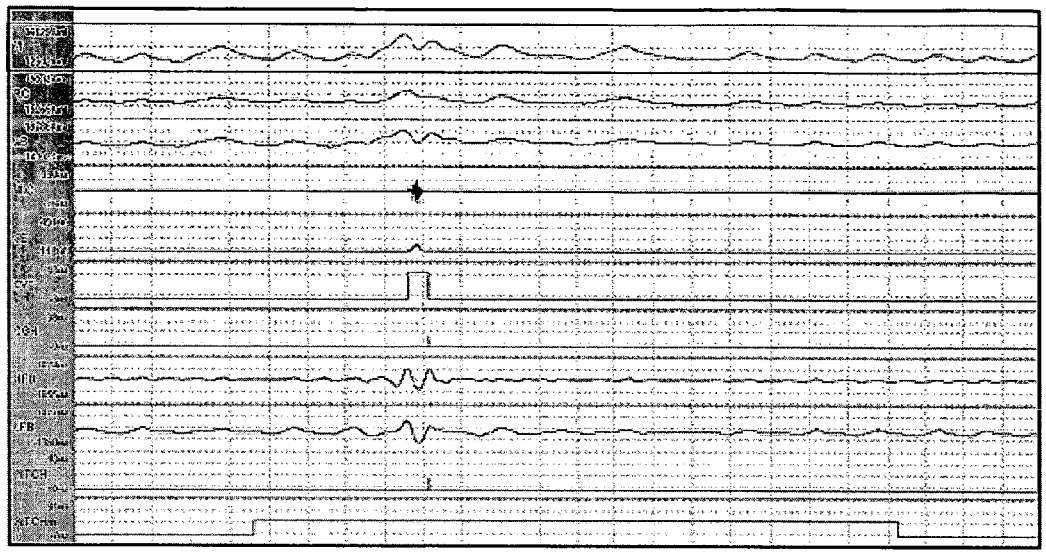
Figure 15B:
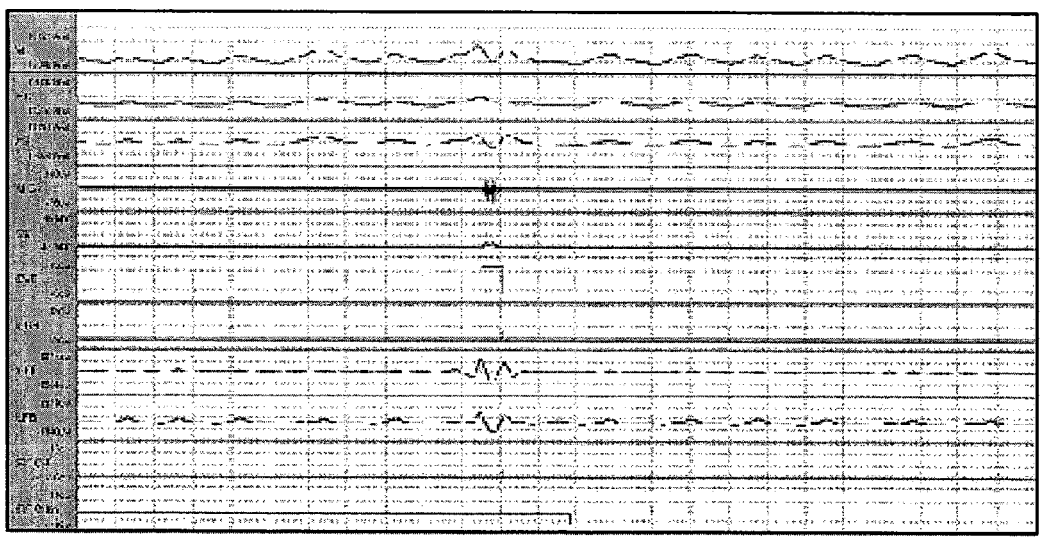

FIGS. 7A–B illustrate an example of the relation of the CAI index on pulmonary function and an example of the lack of a similar relation in the prior art;

FIG. 8 illustrates an exemplary cough signal;

FIG. 9 illustrates methods of cough detection;

FIGS. 10A–B illustrate preferred filter responses;

FIG. 11 illustrates exemplary data recorded during a cough;

FIG. 12 illustrates methods of pitch determination;

FIGS. 13A–D illustrate an example of pitch determination;

FIGS. 14A–B illustrate examples of coughs in a subject with COPD;

FIGS. 15A–B illustrate examples of coughs in a subject with CF; and

Figure 16A:
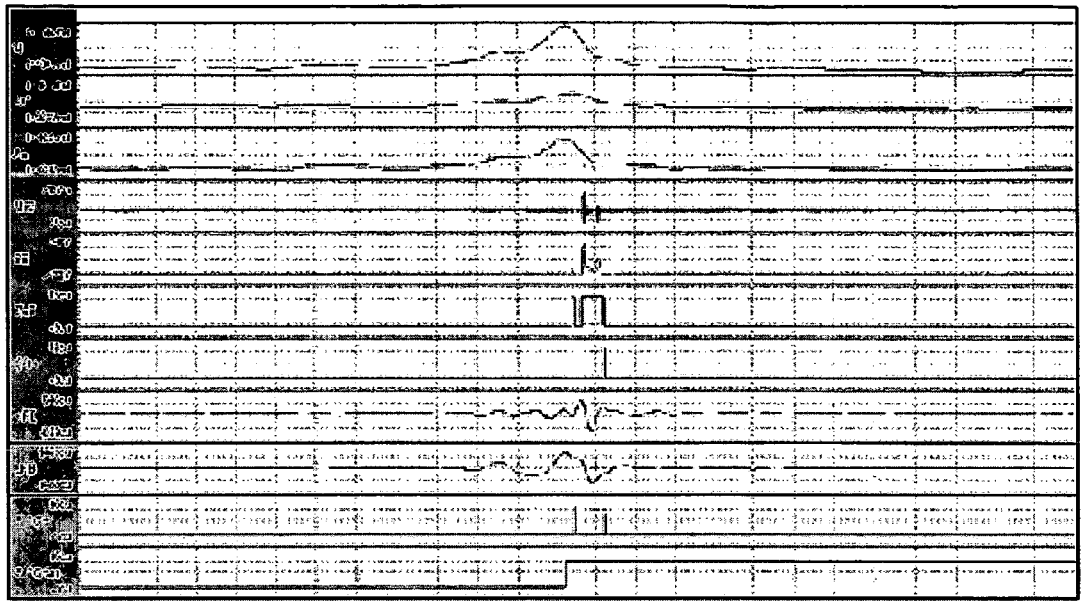
Figure 16B:
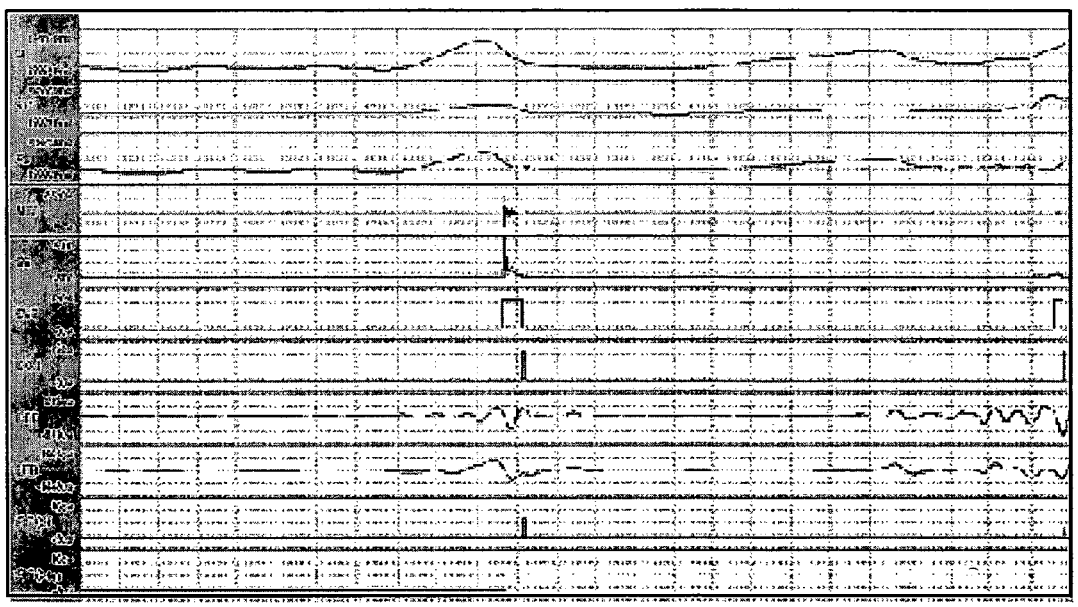

FIGS. 16A–B illustrate exemplary coughs in a subject with post-infectious cough (PIC).

5. DETAILED DESCRIPTION OF THE PREFERRED EMBODIMENTS

Preferred embodiments of the systems and methods of this invention are described in the following. In the following, and in the application as a whole, headings are used to clarity and convenience only.

5.2 Systems and Methods of this Invention

Figure 2:
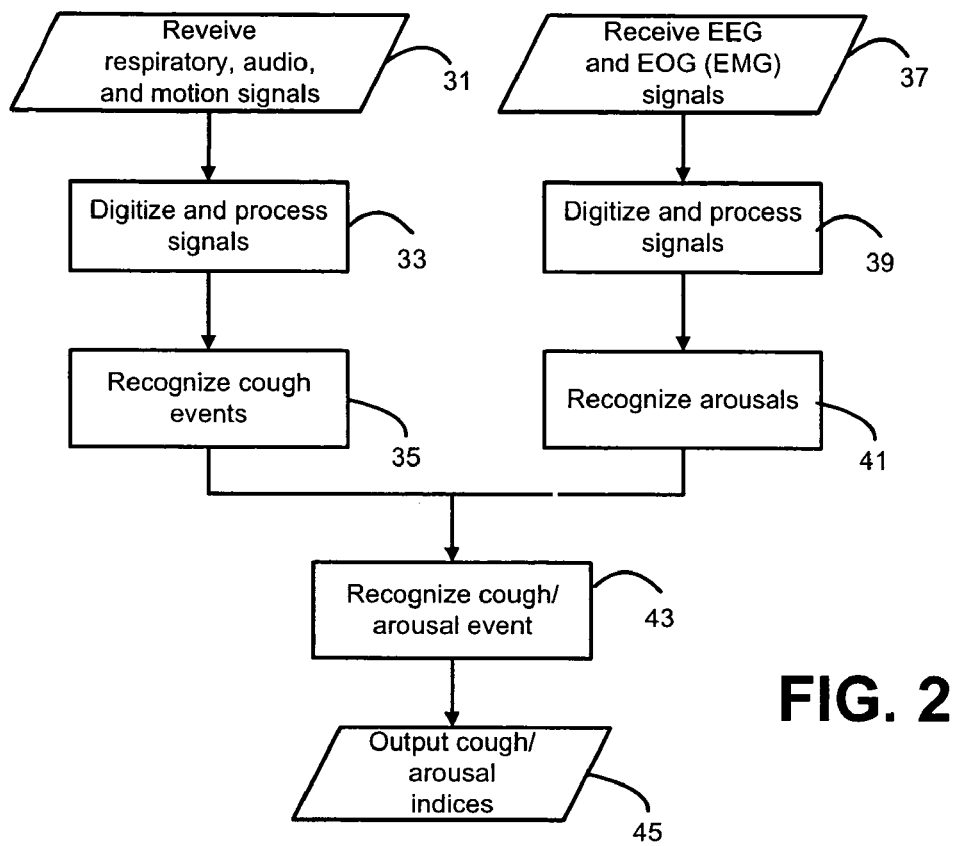
FIG. 2 illustrates general methods of this invention.

FIG. 2 generally illustrates the methods of this invention. Briefly, these methods process and combine two separate streams of physiological data in order to determine novel cough-arousal indices. Subject respiratory, audio, and motion data 31, after pre-processing 33, are used in an objective and automatic procedure 35 to detect occurrences of subject coughs. Subject electroencephalogram (EEG) and electrooculogram data (EOG) (generally, selected electromyogram (EMG) data) 37, after pre-processing 39, are used in an objective and automatic procedure 41 to detect occurrences of subject arousals. Occurrences of recognized coughs and arousals are correlated 43 and the determined cough-arousal and cough-disturbance indices 45 are output. These steps and accompanying systems are described in more detail below.

5.2.2 Recognition of Cough Events

Data processed by this invention is preferably obtained by a wearable monitoring garment, such as garment or shirt 1 illustrated in FIG. 1, which is sufficiently comfortable and unobtrusive so that subject sleep is (substantially) not disturbed. Such a garment carries, has embedded, or integrally included sensors for gathering necessary subject monitoring data, and permits physiological recording during sleep in a home setting of up to a full night's duration and/or daytime recordings in an unrestricted ambulatory setting.

This garment is a preferred example of the monitoring equipment used to provide data for this invention. It does not limit the invention, and in other embodiments the data processed by this invention can be gathered by other sensor technologies known in the art, and by other dispositions and arrangements of such sensors on the monitored subject. However, for conciseness only, the following description is largely in terms of this preferred embodiment of the monitoring garment and associated system components.

Respiratory, audio, and motion signals 31 are obtained, respectively, from inductive plethysmographic (IP) respiratory sensor bands 5 and 7 (or other sensor types providing respiratory rate and volume information), one or more accelerometers and the like for sensing body posture and motion, for example exemplary accelerometer 11 illustrated as within the shirt, and one or more microphones for detecting cough sounds, such as throat microphone 14. Garment 1 (also referred to herein as a "shirt") is made of stretchable material that fits sufficiently snugly to expand and contract with a subject's body so that embedded IP sensor bands (which, for respiratory measurement, are known as respiratory inductive plethysmographic, or RIP, bands) can measure cross sectional areas or circumferences of the subject's torso. One RIP band is adequate, but preferably two RIP bands are used: band 5 at the level of the rib cage, and band 7 at the level of the abdomen. Details of IP technology (and of alternative sensor technologies known in the art) are described following Sec. 5.3 and in the references included therein.

EMG and EOG signals 37 are obtained from EEG and EOG sensors, such as single bipolar (parietally-located) EEG sensor 15 and single lead EOG sensor 13. The EEG and EOG sensors are preferably in electrical communication with shirt 1, for example by means of conductive connector 17. Additional sensors, optional for this invention, may be in or in communication with the shirt, and include pulse oximeters, capnographs, EEG electrodes (illustrated at 9a and 9b), and the like. In the hospital, clinic, or laboratory, other signals may be obtained from a wide range of physiological sensors.

Associated locally with preferred garment 1 is local data recording unit 3 operatively connected to subject sensors of the garment by data cable 2 (or by short range radio link). Data recoding unit 3 is preferred for ambulatory use and is preferably compact and lightweight so that it can be worn on a belt, put in a pocket, or embedded in shirt 1. This unit stores sensor data with sufficient accuracy and precision for full medical disclosure and off-line analysis, and may include a touch screen (or other user input facility) for implementing a digital diary whose data may also be transferred to the analysis computer for correlation with the sensor readings.

The methods of this invention are implemented by analysis software that is executed on analysis computers, such as computer 21. Analysis can be done either concurrently with signal recording (online) or at a later time (off line). For offline analysis, sensor data can be transferred from data recording unit 3 to analysis computer 21 on memory card 19, such as a compact flash card. Data may alternatively be transferred by wireless links, such as transmission using cell phone technologies and the like. All or part of this analysis software implementing this invention's methods may be made available as a program product on a computer readable medium, such as optical disk 23. For sleep monitoring, sensors carried by garment 1 can be directly linked to data analysis and storage system 21. Alternatively, a data recording unit for use during sleep can include additional capability and processing at the cost of decreased portability.

Referring again to FIG. 2, initial digitization and processing of sensor data 33 includes as necessary digitization of analog sensor signals, filtering digitized signal to remove noise and artifacts. Further processing of respiratory signals includes calibration and combination of signals from one or more RIP bands into respiratory rate and tidal volume ($V_T$) signals (and, optionally, processing to remove further remaining artifacts), and their analysis to determine baselines and trends. Details of the processing steps described below.

Further processing of microphone data includes identification of lower frequency sound components and their temporal variability which are combined in order to recognize audio events characteristic of coughs. In a preferred embodiment, likely cough events are then identified when the lower frequency sound components exceed determined thresholds for determined times. These thresholds and times are preferably adjusted to reflect the variations of individual subjects.

Next, objective, computer implemented processes 35 combine and correlate preprocessed respiratory, audio, and motion signals in order to recognize likely cough events. These events are recognized when data is indicative of individual forceful exhalations occurring against a partially closed glottis in a single breath. In particular, a likely cough is indicated by respiratory signals with a high expiratory flow preferably substantially above a (temporally) locally-determined baseline expiratory flow. Further, because a cough is an exhalation against a partially closed glottis, they are often associated with sound events having lower frequency components that are substantially constant for a certain time intervals. A further indicator of a likely cough is observation of sound with these characteristics from processed microphone data. Coughs are recognized by the occurrence of a characteristic breath event, and likely coughs are recognized by a coincidence of a characteristic breath event and a characteristic sound event.

Figure 3:
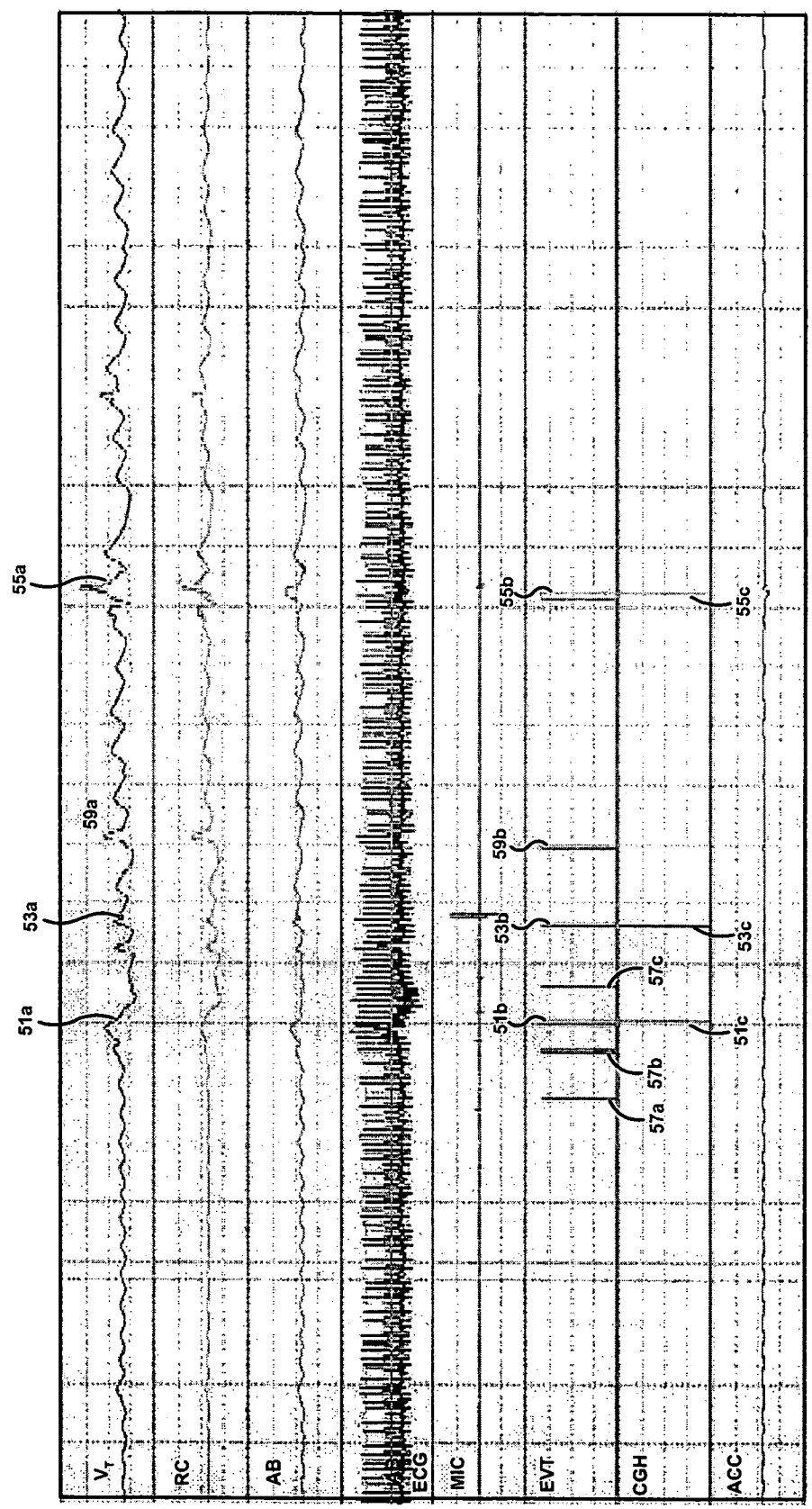
FIG. 3 illustrates an example of cough event detection.

FIG. 3 illustrates likely coughs detected according to these methods. This figure has eight concurrent traces of, from top to bottom, a tidal volume ($V_T$) signal, a rib-cage RIP band (RC) signal, an abdominal RIP band (AB) signal (the $V_T$ is a combination of the RC and AB signals), an electrocardiogram signal (ECG), a microphone signal (MIC), occurrences of recognized sound events (EVT) (recognized from the MIC signal), occurrences of recognized coughs (CGH), and the accelerometer signal (ACC). In all traces, time increases from left to right. The $V_T$ signal is a calibrated combination of the RC and AB signals, and the EVT signal indicates occurrences of sound events from the MIC signal.

FIG. 3 illustrates three recognized likely coughs 51c, 53c, and 55c. Cough 51c is recognized because EVT 51b is coincident with high expiratory flow indicated by the large negative slope 51a in the $V_T$ signal. Similarly, coughs 53c and 55c represent coincidences in EVTs 53b and 55b with large negative $V_T$ slopes 53a and 55a. EVTs 57a, 57b, and 57c are not recognized as coughs because they do not correspond negative slopes in the $V_T$ signals. Finally EVT 59a is not a cough because it corresponds to inspiration (positive slope) 59a in the $V_T$ signal.

5.2.3 Recognition of EEG Arousals

Returning to FIG. 2, received 37 EEG and EOG signals (alternatively, selected EMG signals) are preprocessed 39 and then used to recognize transient arousals 41. Preferred EEG sensor locations, defined using the positioning notation common in the EEG arts, includes central bipolar placements at C4/A1 or C3/A2, and optional bipolar occipital referential placements such as O1/A2, O2/A1 or OZ/A1 or A2. Preferred bipolar EOG electrode placements are LOC/A1 and/or ROC/A2. In alternative embodiments, the EOG signals may be supplemented or replaced by submental or other EMG signals.

The received signals are next digitized and preprocessed 39. Typically EEG and EOG signals exceeding about 50 Hz are of less interest, so adequate signal digitization is 100/sec (the Nyquist frequency); more preferably digitization is at 150/sec or greater, and even more preferably at 200/sec or greater. The digitized signals are next low pass filtered to remove less significant higher frequencies, for example above about 50 Hz. Finally, the signals are processed to provide a spectrogram-type output that is reflective of signal frequency content versus time, preferably according to the standard EEG frequency bands, namely, the alpha band, the beta band, the theta band, the delta band, and so forth. This processing can be by, for example, a bank of time-windowed band-pass filters or a multi-resolution wavelet decomposition, where the filter pass bands or wavelet resolutions are selected according to the EEG frequency bands.

Arousals are then recognized 41 from spectrogram-type output derived from either the central or occipital derivation EEG by, preferably automatically, applying rules derived from standard definitions of EEG arousal. See, for example, Bonnet et al., 1992, EEG arousals: scoring rules and examples—a preliminary report from the sleep disorders atlas task force of the American sleep disorders association, *Sleep* 15: 173–184, 1992. A preferred rule recognizes arousals when the spectrogram reveals an abrupt shift in EEG frequency 3 seconds or greater duration at greater than 16 Hz (e.g., theta, alpha and/or beta frequencies) but without spindles. Because the 3 second criteria is primarily methodological as opposed to physiological, other durations may be used that permit reliable recognition of EEG frequency shifts in the circumstances.

This rule can be qualified according to certain subsidiary rules. Since arousals are considered periodic phenomena disrupting sleep, one subsidiary rule is that an arousal is recognized when a subject has been asleep in any sleep stage for 10 or more seconds, and further that a second arousal is recognized when 10 seconds or more of any sleep stage intervenes between a prior arousal. Generally, 10 seconds is chosen because determination of sleeping versus waking over an interval of less than 10 seconds is less reliable. However, the minimum amount of intervening sleep necessary to score independent arousals will depend on the background EEG and may vary in the circumstances.

A further subsidiary rule makes use of the known classification of sleep according to EEG characteristics into REM (rapid-eye-movement) sleep or NREM (non-REM) sleep (NREM sleep being further sub-classified into sleep stages 1, 3, 3, and 4). In NREM sleep, arousals can be recognized on the basis of EEG characteristics alone. But because bursts of alpha or theta EEG activity are common in REM sleep and may not reflect physiological arousal, reliable scoring of arousal from REM sleep preferably additionally requires that EOG (or EMG) amplitudes increase. However, arousals cannot be scored based solely on changes in EMG amplitude. In essence, if REM sleep is recognized, then such EOG or EMG amplitude increases are required to recognize an arousal.

Further rules useful in recognizing arousals can be derived from the further conditions described in, for example, Bonnet et al.

5.2.4 Recognition of Cough/Arousal Events

Referred again to FIG. 2, cough-arousal events are recognized 43 during sleep when a recognized cough 35 is detected in association with a recognized EEG arousal 41. A cough and an arousal are associated if the cough occurs during the arousal; also a cough and an arousal are associated if the cough occurs within a time window that includes an arousal. A preferred time window precedes the arousal and has a length of approximately 30 sec. (or up to approximately 1 min). Another further preferred time window is approximately 30 sec. (or up to approximately 1 min) subsequent to the arousal. Other suitable time windows can be determined for individual subjects. A cough is not associated with an arousal if it does not occur during an arousal or during a time window associated with an arousal.

Figure 4:
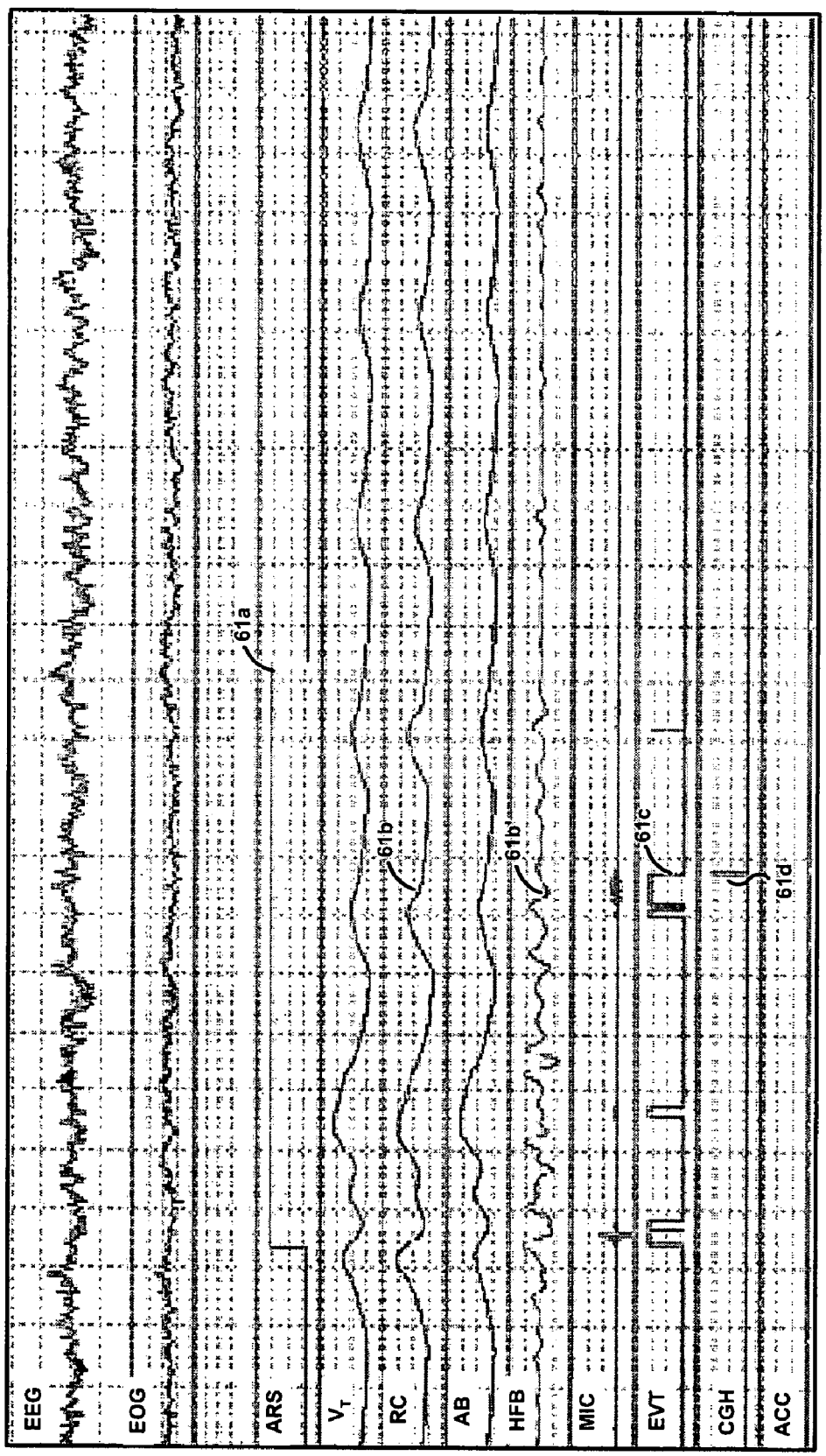
FIG. 4 illustrates an example of cough-arousal detection.

FIG. 4 illustrates an exemplary cough-arousal event. This figure has eleven concurrent traces of, from top to bottom, an EEG signal (EEG), an EOG signal (EOG), recognized arousals (ARS), a tidal volume ($V_T$) signal, a rib-cage RIP band (RC) signal, a abdominal RIP band (AB) signal, a high-frequency filtered $V_T$ signal (HFB), a microphone signal (MIC), occurrences of recognized sound events (EVT), occurrences of recognized coughs (CGH), and the accelerometer signal (ACC). In all traces, time increases from left to right. Cough 61d is recognized as the coincidence of forced expiration 61b with sound event 61c. And because cough 61d occurs in association with (here, during) an EEG arousal 61a, a cough-arousal event is recognized. Forces expiration 61b is more apparent at 61b' in the HFB signal from which low frequency components have been removed. It is also preferably to monitor accelerometer data from a subject. High pass filtering this data provides information on subject motion; low pass filtered data provides information on subject posture. Because motion and/or posture change can cause artifacts in sensor signals, it is advantageous to discard those coughs and/or arousals associated with motion and/or posture change The cough-arousal index (CAI) is then determined as the number of cough arousal events (associated coughs and arousals) per hour (or per other appropriate time period) during sleep. The cough disturbance index (CDI) is determined as the number of coughs per hour (or per other appropriate time period) during sleep that are not part of a cough arousal event (that is, are associated with an EEG arousal). The sum of the CAI and the CDI is the total number of coughs per hour.

These indices are output for use by the monitored subject and monitoring personal. For example, the monitored subject may adjust medication doses so that the CAI is less than an acceptable threshold, or within an acceptable range so that abnormalities in the subject's sleep architecture are adequately reduced. Medical monitoring personnel may monitor CAIs and CDIs of a test population in the course of drug development, testing, or evaluation.

5.2.5 Cough/Arousal Index Examples

The systems and methods of this invention, characteristics of disordered sleep, and the clinical significance of the CAI have been ascertained by the following measurements.

Ten patients with mild to severe COPD were monitored in their homes performing their normal daily activities (including sleep) using the LifeShirt® monitoring system from VivoMetrics, Inc. (Ventura, Calif.). The LifeShirt system implemented the preferred monitoring garment and data recorder described above. In particular, the monitoring garment included an RC and an AB RIP band sensors, a modified limb II ECG sensor, an accelerometer sensor filtered for posture and movement, a contact microphone sensor at thyroid cartilage to identify cough sounds. During sleep, data from associated EEG and EOG sensors was also recorded. This physiological monitoring data was processed by the preferred methods also described above. In addition, video (with audio) tape recordings were used to validate the preferred automatic cough recognition. A sensitivity of 0.78, a specificity of 1.0, and an accuracy of 0.99 were observed.

Figure 5:
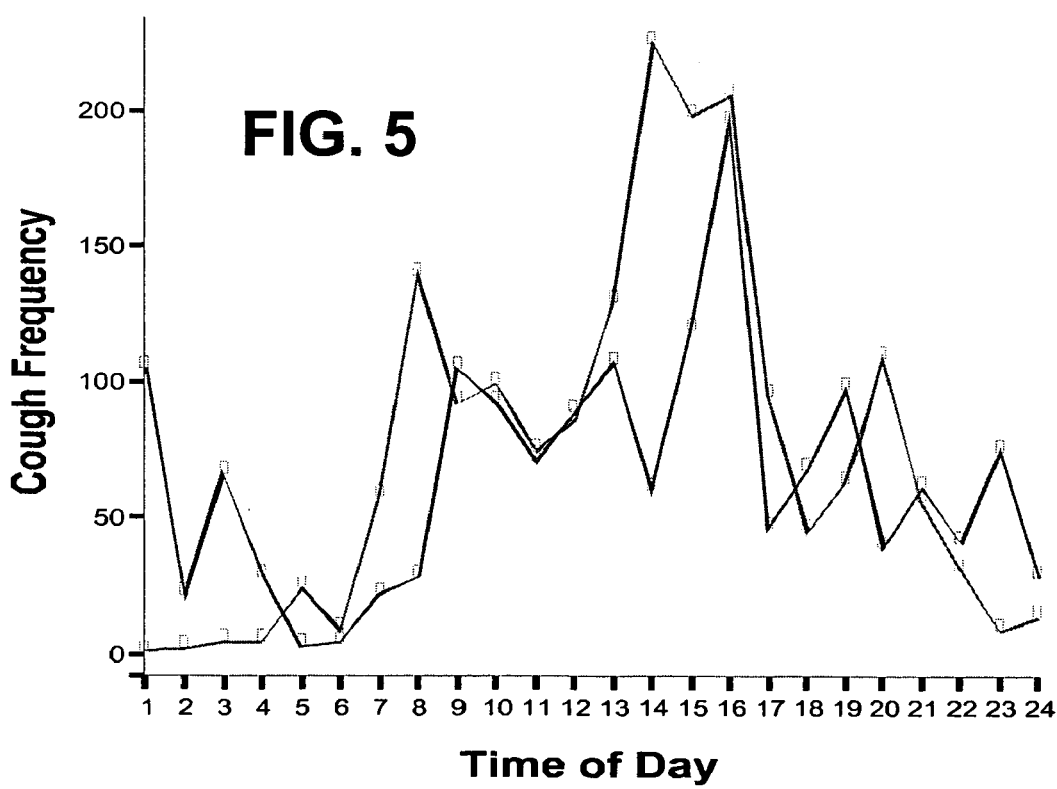
FIG. 5 illustrates an example diurnal cough variability in a subject with COPD.

Results of these measurements include the following. First, FIG. 5 illustrates mean cough frequency per hour throughout each of two days. Cough frequency followed similar circadian patterns on both days, being characterized by cough frequency peaks at approximately 8:00 AM and during approximately the 2–4:00 PM period. Nocturnal cough occurred at a significant frequency throughout most of the night except the early morning. A number of these nocturnal coughs, one of which was illustrated in FIG. 4, occurred during an EEG arousal or within a permissible time window associated with an arousal, and thus contributed to subjects' CAIs (other coughs being counted in the CDI).

Next, sleep was staged into NREM (stages 1–4) and REM sleep using the previously described rules to evaluate the recorded EEG signal, and the number of coughs during each sleep stage ascertained. FIG. 6 illustrates these measurements: the stippled dark bars indicate the mean number of coughs during the sleep stages in the COPD patients; the black squares indicate mean time duration the COPD patients spent in each sleep stage; and the open rectangles ("REF") indicate mean time normal, healthy age-matched controls spend in each sleep stage. All values are means with standard errors of the means being conventionally indicated by error bars (appearing as "I's"). This figure shows that these COPD patients experienced cough evenly distributed throughout both stages 3 and 4 of NREM sleep and also REM sleep. However, during NREM stage 1, coughs were somewhat increases; and during NREM stage 2, an exceptional number of coughs occurred. Thus, nocturnal cough occurred most frequently during the lighter sleep stages, and hence these COPD patients spent a greater than normal percentage of time in stage 1 sleep.

Thus, nocturnal cough is likely to be preventing these COPD patient from progressing naturally to deeper sleep stages, leading a disruption of sleep architecture in which an unusual percentage of time is spent in stage 1 and 2 sleep. This disruption is likely to adversely affect the daytime performance, decrease quality of life, and perhaps lead to further problems. This confirms the importance of monitoring and treating nocturnal coughs in susceptible subjects.

Further, the CAI was determined for these monitored COPD patients according to the previously described methods, and each patient's CAI was correlated to that patient's percent predicted peak expiratory flow. The percent predicted expiratory flow which is the percentage ratio of a patient's $FEV_1$ to the $FEV_1$ predicted for normal, age-matched controls, is a known measure of airway obstruction useful in monitoring COPD. FIG. 7A illustrates the results of this comparison: a bivariate fit of percent predicted peak expiratory flow with CAI shows a correlation strength of 0.64 at a significance of 0.05. This correlation confirms the utility of the CAI as a clinically variable linking observed pulmonary function and sleep quality.

It is significant that the measurements and indices of this invention are determined objectively by computer-implemented methods. These measurements do not rely on patient questioning and recollection. In contrast, prior determinations of cough and disordered sleep have relied on such patient recollection and reporting, both of which are known to be unreliable. FIG. 7B illustrates another evidently unreliable prior art comparison of percent predicted peak expiratory flow with an index of cough. The cough index used, in the absence of long term recording of cough occurrences, was sensitivity to capsaicin, a cough inducing irritant which is an active component of peppers and used in scale of gustatory spiciness. In comparison with FIG. 7A, which demonstrates an objectively-determined cough cough-arousal index that strongly correlates with percent predicted peak expiratory flow, this figure demonstrates no observable correlation in either COPD or asthma patients between percent predicted peak expiratory flow and this cough index.

5.3 Preferred Systems and Methods

This subsection further additional details of the previously described systems and methods. 5.3.2 Preferred Systems Respiratory data preferably reflects time-varying cross-sectional areas of the subject's rig cage, and also advantageously the subject's abdomen. Techniques of signal processing and pattern recognition with reference to established physiological models (such as the two-compartment model of respiratory volumes) can yield indicia or measures of physiological functions and times of occurrences of physiological events. For example, it is possible to obtain respiratory rate, tidal volume indicia, indicia of cardiac stroke volumes, occurrence times of respiratory apneas, and the like.

One preferred sensor technology fur such measurements is inductive plethysmography (IP). This technology has been clinically confirmed to provide reliable, semi-quantitative and quantitative data on cardiac and respiratory functions. Briefly, IP measures the inductance of conductive loops (generally, configured as sensor bands) that are placed at various levels about the thorax, abdomen, and other body structures of a monitored subject. Such time-varying loop inductance measurements reflect primarily the time-varying cross-sectional areas enclosed by these loops.

However, this invention is not limited to IP-based sensors, and alternative sensor technologies can be employed. Possible alternative sensor technologies make, similar to IP-based sensors, measurements reflective of cross-sectional areas, or circumferences, or their geometric equivalents (for example, stress or strain), at one or more levels through the thorax, abdomen, or other body structures. Their signals can be processed by methods already developed for IP sensor signals. For example, alternative sensors can be based on thread and fabric technologies being and to be developed: a sensor may measure the resistance of conductive threads having strain-dependent resistance may be incorporated into garments or bands; or a sensor may measure by optical or electrical means the local strain of a fabric woven so that local strain is reflective of circumferential overall strain. For another example, alternative sensors may use energy radiation (such as ultrasound, or electric, magnetic, or electromagnetic fields) to measure geometric parameters (such as distances) through body structures.

Other sensors may be incorporated in this invention as needed and when available. These can include, for example, sensors for chemical exposures (CO, $CH_4$, and the like), sensors for biological hazards (various kinds of radiation, of organisms, and the like), and other sensors. Details of IP-based wearable sensors and garments are disclosed in the sensor and garment patents and/or the cardiac function patents.

Physiological sensors are preferably disposed on monitored subjects in various kinds of garments, for example, in bands, or in partial-shirts, or in shirts, or on partial body suits, or in full body suits, and the like that are unobtrusive, comfortable, and non-restricting fabric. This invention includes a variety of such garments and sensor dispositions therein, the particulars of which depend primarily on the type and extent of physiological monitoring. These garments are preferably designed to allow sleep and/or ambulatory activities without significant disturbance Details of the preferred IP technology, its disposition in garments, its processing and interpretation, and certain closely allied sensor technologies can be found in the following U.S. patents and applications (the "IP patents") currently assigned to the current assignee of this application. All of these patents and applications are incorporated herein by reference in the entireties herein for all purposes. U.S. patents (the "sensor and garment patents") disclosing IP technology and its disposition in fabrics and garments include, for example, U.S. Pat. Nos. 6,551,252; 6,341,504; 6,047,203; 5,331,968; 5,301,678; and 4,807,640, issued Feb. 28, 1989 (stretchable IP transducer).

U.S. patents (the "data processing and interpretation patents") disclosing processing of IP signals, for example, U.S. Pat. Nos. 6,413,225; 6,015,388; 5,159,935; 4,860,766; 4,834,109; 4,815,473; 4,777,962; 4,648,407; 4,373,534; and 4,308,872. Similar U.S. patent applications includes: Ser. No. 10/822,260, by Coyle et al.; filed Apr. 9, 2004; and Ser. No. 10/457,097. U.S. patents ("cardiac function patents") disclosing processing of IP signals to obtain measures of cardiac function include, for example, U.S. Pat. Nos. 5,588,425; 5,178,151; 5,040,540; 4,986,277; 4,456,015; and 4,452,252, and U.S. application Ser. No. 10/107,078.

5.3.3 Methods of Cough Event Recognition

Generally, these methods proceed by recognizing candidate respiratory events from input respiratory parameters including AB, RC, and $V_T$ signals and, optionally, candidate sound events from audio input. Then coughs events are detected from coincident combinations of candidate respiratory events and associated candidate sound events. Types and severity of coughs may be discriminated by the values of the respiratory and sound event parameters.

A First Method for Cough Recognition

The first preferred method for cough detection uses only respiratory data and is thus advantageous where sound data is not available. According to a first cough detection method, coughs must be recognized true breaths with expiratory periods greater than a pre-determined threshold having a range of from 0.25 to 3 secs. A useful and preferred threshold is approximately 1 sec, which may be individualized. Then, true breaths meeting these criteria are recognized as coughs if their peak expiratory flow (PEF) is greater than a pre-determined threshold of the running median baseline PEF value as determined from a leading, two minute window. A preferred PEF threshold is between 100 and 1000% or greater of the running median baseline PEF value; for many subjects, a PEF threshold greater than approximately 250% results in adequate cough recognition. The threshold can be individualized to particular subjects using past monitoring data.

FIG. 8 illustrates actual subject data containing coughs 94 and 98. PEF is determined from the dV/dt (labeled dVt/dt) curve as short, rapid exhalations and in which the same two coughs 96 and 102 are readily visible as short sharp exhalations. In this example, PEF for cough 96 is approximately 400% of the running median PEF baseline, while for cough 102, the PEF is approximately 380% of the baseline.

A Second Method for Cough Recognition

The second method for cough detection incorporates sound input as an aid to cough detection and is preferred if sound data is not available. In this subsection and accompanying figures, input data and derived data are often referred to by the following abbreviations:

RC Ribcage (RC) measurements (input data)
AB Abdominal (AB) measurements (input data)
$V_T$ Tidal Volume (method input data derived as described from the RC and AB measurements)
HFB High frequency band pass filtered Vt (derived data)
LFB Low frequency band pass filtered Vt (derived data)
FAB High frequency band pass filtered AB (derived data)
MIC Microphone audio signal recorded from a throat microphone (input data)
SE Microphone audio signal envelope (derived data)
PITCH Maximum significant audio pitch level in a selected time interval (derived data)
PITCHm Mean audio pitch level in selected time intervals (derived data)
EVT Audio event and duration detector (method step)
CGH Cough marker (method output data indicating presence of a detected cough)

Briefly, the Vt is first filtered into high frequency and low frequency components. The AB signal is also filtered into high frequency components. These further are optionally designed to further limit high frequency noise and low frequency movement artifacts. If the filtered signals have peak-to-peak power amplitude, or breath amplitudes (the difference between maximum expiration and maximum inspiration) exceeding a predefined threshold, T, then both respiratory and audio signals are examined in more detail to detect the presence of a likely cough event. If the threshold is not exceeded, a cough event is not likely.

Audio signals (from, for example, a throat microphone) are processed with a speech recognition front-end to determine if an audio event contains voiced or unvoiced speech. Important to this determination is the derived signal PITCHm, which is the mean of pitch values over a finite duration in selected bands, m. This mean level should increase significantly if the subject is speaking or engaged in a conversation, and not increase in the case of a cough. The pitch value is computed by measuring the peak-to-peak power present in the Cepsturm or Mel Frequency Cepstral Coefficients (MFCCs). Another important derived signal is the PITCH signal. Output from audio signal processing are pulses, as illustrated by the EVT trace in FIG. 11, with timing and duration equal to that of significant audio events detected in the input sound data.

In the absence of a sound event, no cough is detected. If a sound event is present, its duration determines which filtered respiratory signals should be applied to the cough signature detector. If the duration of the sound event is relatively long (that is longer than the median significant sound event), e.g., >=600 msec, the low frequency band pass filtered respiratory data, LFB, is analyzed by a cough signature detector. If the audio duration is relatively short (that is longer than the median signification sound event), e.g. <=600 msec., the high frequency band pass respiratory data, HFB, is analyzed. This signal selection has been found to lead to adequate filtering of movement and motion artifact so that cough signatures may be more clearly detected.

FIG. 9 illustrates in detail this second method for cough detection. The tidal volume trace $V_T$, which has been previously determined as the linearly weighted sum of the RC and AB bands, is first passed through 2 FIR band pass filters in parallel and the peak power (as reflected by the maximum of the filtered signal) is measured to determine the existence of a possible cough event if the peak power exceeds threshold T. Filters for the input respiratory signals are preferably of the finite impulse response (FIR) design, although infinite impulse response (IIR) filters with a minimal phase shift or time delay may be used. Here, respiratory signal phase must be sufficiently unperturbed so that it remains temporally coincident with the corresponding audio signals.

A filter length of 1024 was determined as the preferable in order to achieve the sufficiently sharp frequency and flat phase characteristics illustrated in FIG. 10A for the high frequency band filter in FIG. 10B for the low frequency band filter. Table 1 lists the parameters of these preferred respective filters, which have been selected to filter to the extent possible subject physical movement while retaining sufficient respiratory movement captured from the rib cage and abdomen (RC and AB).

TABLE 1

FIR filter design parameters.

| Signal | Stop 1 Freq (Hz) | Pass 1 Freq (Hz) | Stop 2 Freq (Hz) | Pass 2 Freq (Hz) | Stop 1 Attenuation (dB) | Pass Attenuation (dB) | Stop 2 Attenuation (dB) |
|---|---|---|---|---|---|---|---|
| LFB | 0.4 | 0.5 | 4.9 | 5.0 | 80 | 0.5 | 80 |
| HFB | 1.0 | 1.1 | 4.9 | 5.0 | 80 | 0.5 | 80 |

Next the peak-to-peak power is measured and compared to a threshold. The peak-to-peak power is preferably taken to be the difference between the maximum on a positive going signal to the minimum on a negative going signal. If it meets a predetermined threshold, a candidate cough event is considered likely present in the filtered respiratory signal. If this threshold is not met, a cough event is not considered likely and no further processing of this portion of the signal is performed. Signals LFB, HFB, and FAB are measured to make this determination. Signal FAB is the filter residual from the AB filtered trace, and is advantageous in the event that RC and AB are out of phase and a have a subtraction effect on Vt decreasing the true effort in the bands.

The threshold T is preferably selected so that normal breaths are not passed for further examination. It can be a median or mean or other measure the subject's current breaths. Alternatively, a fixed threshold can be used. Generally, approximately 200 ml expired volume is suitable for resting or sleeping subjects. Preferably, a fixed threshold is selected for a particular subject population or more preferably for a particular subject, in which can a wide range of volumes may be suitable. A threshold can also be selected as a percent of the subject's current expiratory volume.

The next steps process the input microphone signal (MIC). FIG. 11 illustrates at an enlarged scale an exemplary sound envelope—trace SE—derived from an exemplary microphone input—trace MIC. The sound envelope is preferably down sampled to the same sample frequency as all respiratory bands, that is preferably 50 Hz to minimize the effects of filter residuals and derivations of the respiratory signals (also preferably sampled at 50 Hz). This down sampling involves averaging every 30 samples from the microphone stream, which is initially sampled at 1500 Hz to yield the 50 Hz sound envelope. The figure also illustrates the determined audio event—trace EVT—and the accompanying high frequency filtered Vt signal—trace HFB.

Next, the sound envelope signal is processed for audio event detection and duration determination. The start of an audio event is recognized when the sound envelope passes a threshold determined to be a selected multiple of the calibrated background noise threshold. Preferably, the noise threshold is calibrated from local or long term microphone recordings (up to 240 hours has been used). This signal is scaled to a variation of between +1 and −1 and represents a level of 30 (arbitrary units) on the sound envelope signal scale. An advantageous event threshold has been found to be twice the noise threshold, or a value of 60. The audio event ends when sound envelope drops back below the noise threshold (here, a value of 60). Use of a throat microphone minimizes background noise. An audio event is marked in the EVT trace as a pulse of amplitude 10 (arbitrary units) and duration equal to the length of the audio event. If no audio event if detected, a cough is not likely to be present and processing of this portion of the signal ends.

A cough signature is found by combining the processed respiratory and the processed sound signals. If a possible audio event coincides with a possible respiratory event, one of these signals is selected depending on the audio duration and further analysed for further cough signature detection. Having determined the duration of a significant audio cough event either the LFB signal or HFB signal is further analyzed for the presence of a cough signature. To select the frequency band to analyze, the audio event duration is measured. For short audio event durations, that is for events less than about 600 ms (preferably, individually adjusted), the HFB signal is analyzed, because shorter coughs as revealed by the shorted sound even time are likely to have higher respiratory frequency components (in order to expire a the shorter time). Conversely, audio events of longer time duration are likely to have respiratory signals of lower frequency signals so that the LFB signal is chosen for further cough signature detection.

A typical cough signature is shown in the HFB trace of FIG. 11. A cough signature preferably has a sharp expiration (corresponding to a high peak expiratory flow) followed by a sharp inspiration in either the HFB or LFB traces or both, that occur in association with an audio event classified as a cough event. The lowest sample value the HFB or LFB traces is preferably located close to the center region of the associated audio event. The center region is defined as those times that are greater than 33% of the audio event duration from the start of the audio event and less than 33% of the event duration from the event end. Furthermore, this minimum value must exceed the T value, which may be selected and calibrated based on the mean breath volume for the particular subject (measured during times of identified quite or relaxed breathing).

Moreover, the slopes of the HFB or LFB traces (and the gradients of these slopes) on either side of the minimum are preferably within the following constraints. First, difference between each sample $[x(n)-x(n-1)]$ should therefore be negative before the center of the signature and positive after the center and before the end. Next, the signature should be reasonably symmetrical with similar slopes on each side of the center sample of minimum. The end points of each slope on either side of the center sample or minimum are the points where the signal reaches maximum amplitude before starting to decrease. These end points should not exceed a time duration greater than 50% of the event time duration past the end of the event or before the end of the event. By applying these tight constraints, the possibly of falsely detecting a cough like event as a cough has been found to be reduced. Alternatively, thresholds may be specified that must be exceeded by the peak expiratory flow and the succeeding peak inspiratory flow.

If the cough signature detector determines that a cough is not likely, further processing of this portion of the signal ends. If a cough signature is detected, in one embodiment, the likely presence of a cough is finally output. However, in a preferred embodiment, the sound signal is further analyzed to separate cough sounds from speech sounds. The further analysis converts the input audio waveform to a compact parametric representation (preferably a form of frequency versus time representation) so that cough sounds may be distinguished from speech sounds, the former generally having lower frequencies and the latter higher frequencies. Accordingly, a frequency-related threshold may be defined in the compact representation so that signals below the threshold are likely to be cough sounds. If the pitch exceeds what is likely for a cough, P, the event is not considered to be likely to be a cough. If the pitch determination is satisfactory (less than P), this embodiment output the likely presence of a cough.

The following summarizes these tests. A candidate event that has the respiratory signature of a cough is not considered to be a cough if the associated sound event is determined not to include cough sounds and/or to include speech sounds. Conversely, a candidate event that has the sound signature of a cough is not a considered to be a cough if the associated respiratory event does not have cough characteristics. An alternate test depending on pitch accepts a sound event as cough if the signal power below the cough-speech threshold increases even if there is signal power above the cough-speech threshold. A candidate event is also not considered a true cough if the PITCH value is above a certain threshold (mel-frequency threshold of 1.5–2). Even if the PITCH value is just below this threshold, a candidate event will not be considered a cough if the PITCHm value is above this threshold, where PITCHm is the average of all PITCH values within a predefined time duration. If the average of these PITCH values is above this threshold, it is implied that there is speech before and after this event, and therefore this event is probably speech.

Figure 13A:
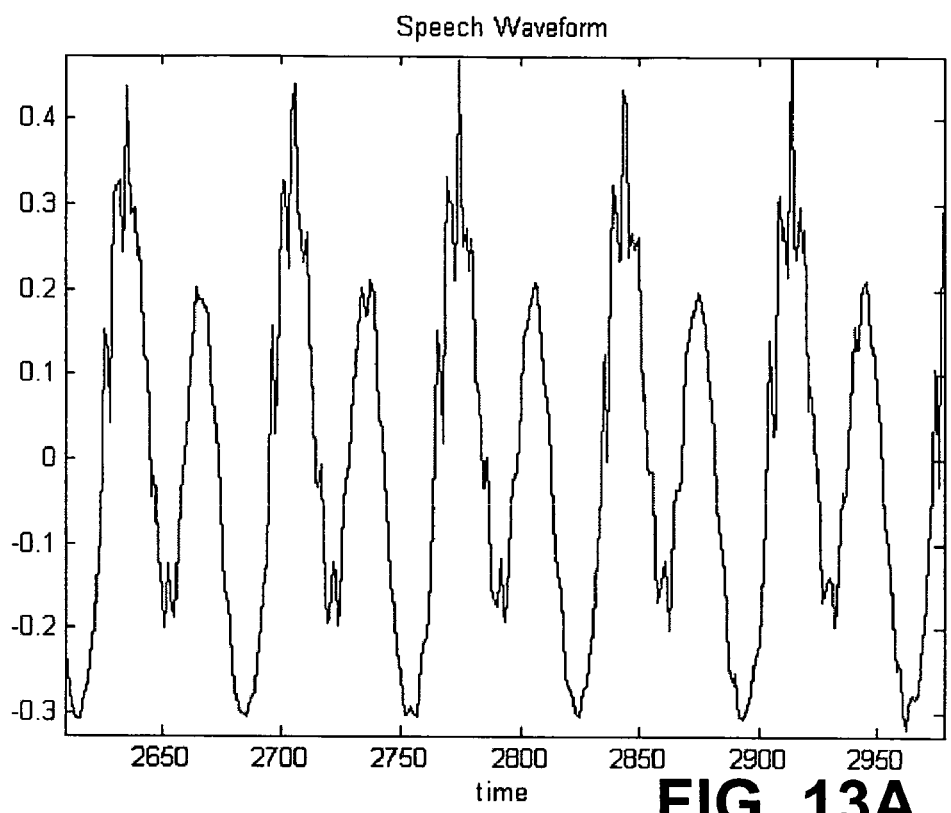

For these further tests, the characteristics of a speech audio signal are considered to be stationary over time increments of approximately 10 msec., and the pitch of the audio signal is therefore analyzed over such segments of such time duration. An example of the stationary portion of a speech signal is shown in FIG. 13A (time in msec.). Even though over longer time durations, speech signal characteristics certainly change to reflect the different audio sounds being generated, short-time spectral analysis is a known way to so characterize audio signals.

Several techniques are known for parametrically extracting and representing the pitch characteristics of an audio signal, such as Linear Prediction Coding (LPC), Mel-Frequency Cepsturm Coefficients (MFCC), and others. MFCCs have been found to be the preferable method. Generally, MFCCs are based on the known variation of the human ear's critical bandwidths so that these coefficients are expressed in a mel-frequency scale, which is linear at frequencies less than 1000 Hz and logarithmic at frequencies above 1000 Hz. These filters capture the phonetically important characteristics of speech.

MFCC Determination

FIG. 12 is a flowchart of the preferred process of computing MFCCs and is now described in this subsection. It process an audio input sampled at 1500 Hz, a sampling frequency chosen to resolve speech and cough components. The first step in this process, the frame blocking step, blocks the continuous audio input signal into frames of N samples, with adjacent frames being separated by M samples (M<N). The first frame consists of the first N samples. The second frame begins M samples after the first frame, and overlaps it by N−M samples. Similarly, the third frame begins 2M samples after the first frame (or M samples after the second frame) and overlaps it by N−2M samples. This process continues until the entire audio has been blocked into one or more frames. Preferred blocking parameters N and M are N=64 (which is equivalent to 40 msec. windowing and facilitates the fast radix-2 FFT) and M=32.

The windowing step windows each individual frame to minimize signal discontinuities at frames boundaries. Spectral distortion is minimized by using a continuous and smooth window to taper the signal to zero at the beginning and end of each frame. If a window is defined as w(n), $0 \leq n \leq N-1$, where N is the number of samples in each frame, then the result of windowing is the signal $$y_l(n) = x_l(n)w(n), 0 \leq n \leq N-1 \quad (1)$$

The Hamming window is preferably used in this invention. It is defined as:

$$w(n) = 0.54 - 0.46 \cos\left(\frac{2\pi n}{N-1}\right), 0 \leq n \leq N-1 \quad (2)$$

The next processing step is the Fast Fourier Transform, which converts each frame of N samples from the time domain into the frequency domain. The FFT is a well known algorithm for implementing the discrete Fourier transform (DFT), which is defined on the set of N samples $\{x_n\}$, as follows:

$$X_n = \sum_{k=0}^{N-1} x_k e^{-2\pi jkn/N}, n = 0, 1, 2, \ldots, N-1 \quad (3)$$

Figure 13B:
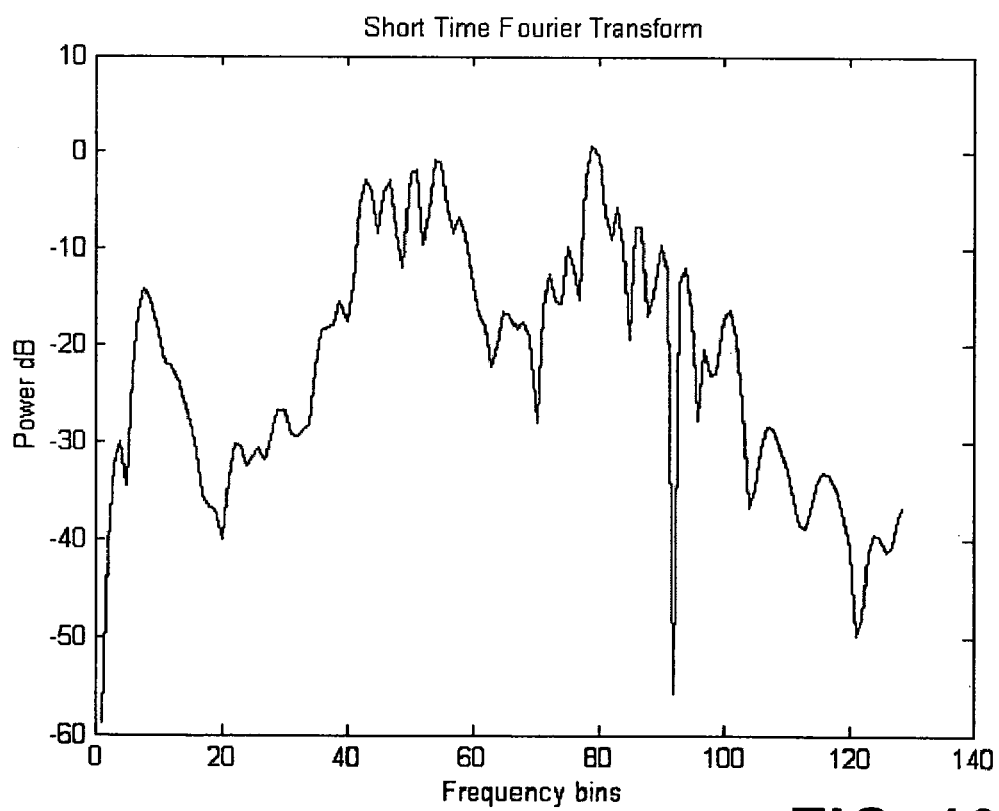

In general $X_n$'s are complex numbers. The resulting sequence $\{X_n\}$ is interpreted as follows: the zero frequency corresponds to n=0, positive frequencies $0 < f < F_s/2$ correspond to values $1 \leq n \leq N/2-1$, while negative frequencies $-F_s/2 < f < 0$ correspond to $N/2+1 \leq n \leq N-1$. Here, $F_s$ denotes the sampling frequency. The result of this step is often referred to as spectrum or periodogram. FIG. 13B illustrates the spectrum or periodogram of the signal of FIG. 13A.

The next step is mel-frequency wrapping. Psychophysical studies have shown that human perception of the frequency contents of sounds does not follow a linear scale. Thus for each tone with an actual frequency, f measured in Hz, a subjective pitch is measured on a scale called the 'mel' scale, which has a linear frequency spacing below 1000 Hz and a logarithmic spacing above 1000 Hz. As a reference point, the pitch of a 1 kHz tone, 40 dB above the perceptual hearing threshold, is defined as 1000 mels. Therefore the following approximate formula computes mels. for a given frequency f in Hz:

$$\text{mel}(f) = 2595 * \log_{10}(1 + f/700) \quad (4)$$

Figure 13C:
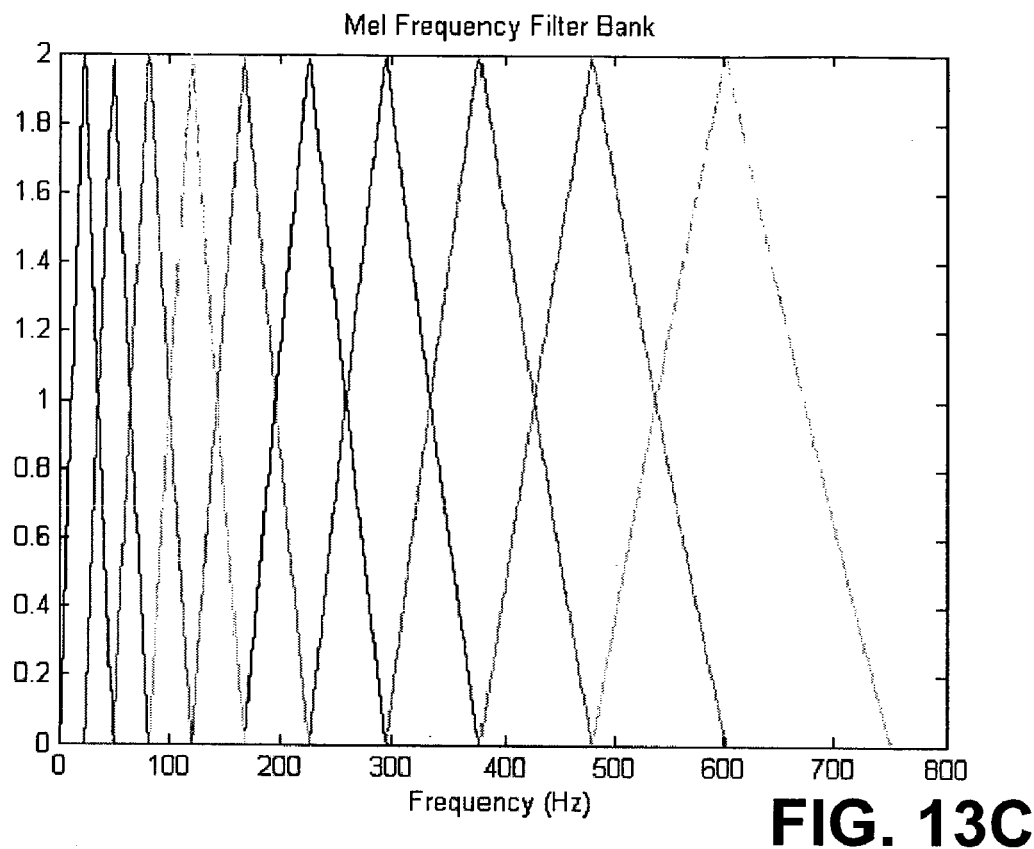

Simulating the subjective audio spectrum commonly is done by a filter bank, with filters spaced uniformly on the mel scale as illustrated in FIG. 13C. The filter bank preferably has a triangular band pass frequency response, and the spacing as well as the bandwidth is determined by a constant mel frequency interval. The mel-filtered spectrum of an input signal, $S(\omega)$, thus consists of the output power of these filters when $S(\omega)$ is the input. The number of mel spectrum coefficients, K, is typically chosen as between 18 and 24. Note that this filter bank is applied in the frequency domain, therefore it simply amounts to multiplying those triangle-shape window coefficients of FIG. 13C with the time frequency spectrum of FIG. 13B. In this method, it has been found preferable to apply a K=10 mel scale filter banks to the input signal frequency spectrum due to the low sample rate.

In the final step of cepsturm determination, the log met spectrum is transformed back to time resulting in the met frequency cepsturm coefficients (MFCC). The cepstral representation of the speech spectrum provides a representation of the local spectral properties of the signal for the given frame analysis. Because the met spectrum coefficients (and so their logarithm) are real numbers, they can be converted to the time domain using the Discrete Cosine Transform (DCT). Therefore if the met power spectrum coefficients that are the result of the last step are denoted by $\tilde{S}_k$, k=1, 2, . . . , K, the MFCC's, $\tilde{c}_n$, may be calculated as:

$$\tilde{c}_n = \sum_{k=1}^{K} \log(\tilde{S}_k) \cos\left[(k-1/2)\frac{n\pi}{K}\right] \cdot n = 1, \ldots, K \quad (5)$$

Note the first component, $\tilde{c}_0$, is advantageously excluded from the DCT since it represents the mean value of the input signal that carries little speaker specific information.

Figure 13D:
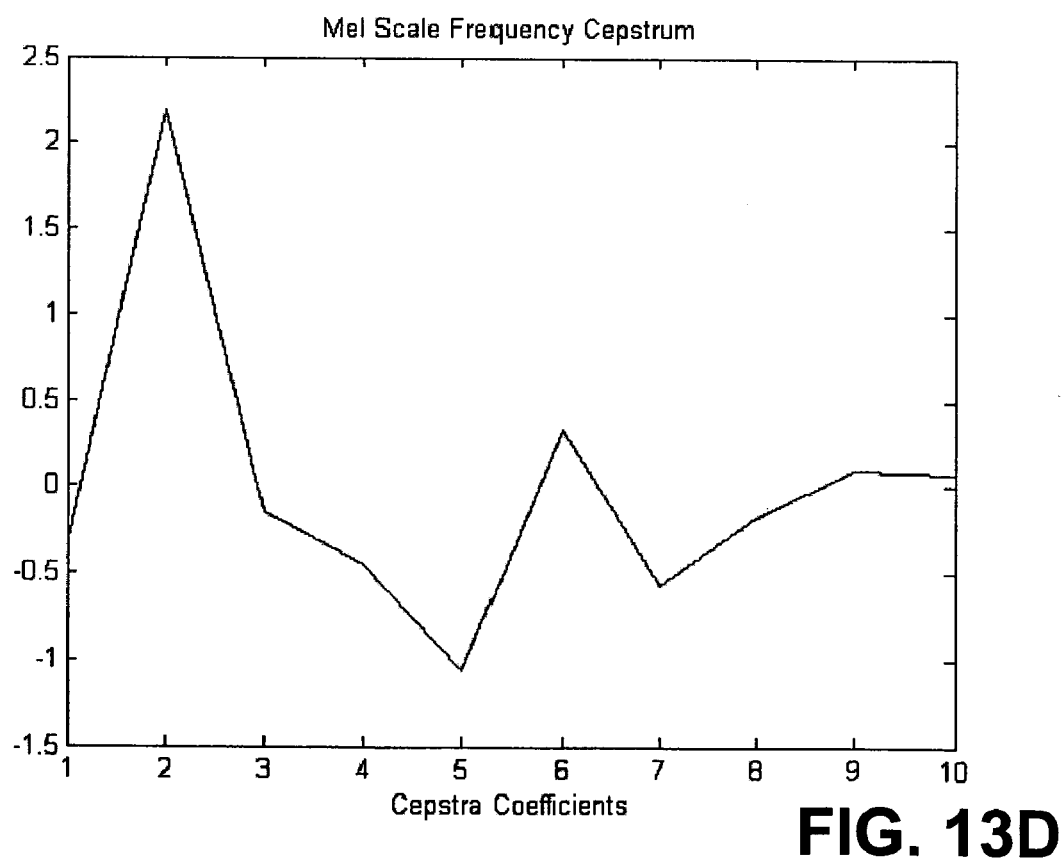

FIG. 13D illustrates the cepsturm output for the speech signal already presented in FIGS. 13–C. Cough and unvoiced speech sounds have been found to generally fall below a me-frequency threshold of 1.5–2. It is evident that voiced speech is present in the exemplary signal because signal power is present above this threshold in the higher pitches. The PITCHm signal can be obtained as a simple mean, or a power-weighted mean, or the like of the mel-frequency spectrum. The PITCH signal can be obtained as the maximum (significant or having 5% or 10% or 20% of the total met power) mel-frequency cepstral coefficient resultant from the discrete cosine transform.

Cough Severity and Classification

Optionally, detected coughs may be analyzed for severity and type. Cough severity events can be analyzed by extracting particular characteristics of the band pass filtered lung volume data, the LFB and HFB signals. The characteristics include the depth or amplitude of the cough signature and the reflex inspiratory drive at the end of the cough signature. Measures that allow for a discrimination of the pathological causes of coughs include a ratio of the depth of cough with the mean expiratory volume calculated on a per subject bases during identified periods of quiet and relaxed breathing. This allows severity to be determined based in the individual calibration and therefore aids in determining lung disease. Further such measures include the rate of change of both expiratory and inspiratory volume during a cough event. Further measures analyze segments of the cough and compare rates of change of volume at different intervals of the cough event.

In simpler cases, the amplitude of these signals (cough volume) and their slope (airflow rate) can be combined into diagnostic criteria for classifying one type of cough from another. These criteria reflect, for example, the different depth of cough and the reflex inspiratory action at the end of the cough event. Appearance of a cough signature in the unfiltered Vt is further indicia of particular severe cough. Using these simpler severity criteria, it has been found that CF coughs can be recognized because they are likely to be of a higher severity; and COPD coughs because they are likely to be of a lower severity. PIC coughs are likely to be of an intermediate severity. Presence of a cough signature in the unfiltered tidal volume trace Vt accompanies coughs of the highest severity.

5.3.4 Cough Examples

Various types of cough signatures and preferred criteria for there discrimination are now described in connection with FIGS. 14A–B, 15A–B, and 16A–B. Chronic obstructive pulmonary disease (COPD) generally refers to a group of pulmonary disorders that lead to progressively worsening respiratory function. Two common causes of COPD that progressively impair airflow to the lungs are bronchitis and emphysema. In chronic bronchitis, the airways are blocked and inflamed, mucus producing glands in the bronchi are enlarged, and an excessive amount of mucus is secreted into the lungs. Therefore, this form of COPD leads to an increased need to cough in order to clear this excessive mucus.

FIGS. 14A–B illustrate COPD coughs that were identified by the systems and methods of this invention as implemented in a software application and confirmed by audio and video recording. The HFB and LFB traces illustrate that the true cough in FIG. 14A is characterized by sharp (short duration and high airflow) expiration followed by sharp inspiration. Further an audio event was detected from throat microphone input that was characterized as having a low pitch and most likely to include cough sounds. FIG. 14B illustrates several non-cough events and one true cough event from a different COPD subject. The non-cough events are seen as low-pitched sound events that lacked accompanying respiratory cough indicia (sharp inspiration and expiration in the LFB or the HFB signals). On the other hand, the true cough event is characterized by associated sound and respiratory events having proper characteristics.

Cystic Fibrosis (CF) is a life threatening multi-system condition that primarily affects the lungs and digestive systems. CF leads to the secretion of sticky mucus obstructing the airways, and causing a need to cough frequently in order to try to clear the mucus from the airways. Coughing can often loosen the mucus allowing easier breathing. FIGS. 15A–B illustrate coughs from two CF patients. It is apparent from examination of the associated traces, especially the HFB and LFB traces, that these coughs are more severe than the COPD coughs, having greater amplitudes and/or higher airflows. Furthermore, the amplitudes are sufficient so that cough signatures are readily identified in the unfiltered tidal volume (Vt) trace.

Post-infectious cough (PIC) is most common after viral infections of the upper respiratory tract. These infections can induce coughing due to persisting inflammation regardless of any increased mucus secretion. FIGS. 16A–B illustrate two examples of PIC coughs. They are seen to be of a severity intermediate between CF and COPD coughs.

The invention described and claimed herein is not to be limited in scope by the preferred embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

A number of references are cited herein, the entire disclosures of which are incorporated herein, in their entirety, by reference for all purposes. Further, none of these references, regardless of how characterized above, is admitted as prior to the invention of the subject matter claimed herein.

What is claimed is:

1. A computer-implemented method for monitoring cough in a subject comprising:
    monitoring data comprising tidal volume data and sound data with a monitoring device responsive to said subject;
    processing said monitored tidal volume ($V_T$) data in order to recognize a respiratory event when a peak-to-peak amplitude of a breath exceeds a threshold;
    processing said monitored sound data in order to recognize a sound event when a sound envelope exceeds a threshold;
    processing each recognized event respiratory to determine if it temporally overlaps a sound event and further to determine if it has an expiration-inspiration pattern characteristic of a cough; and
    selecting as a cough event each respiratory event that overlaps a sound event and that has said characteristic expiration-inspiration pattern.

2. The method of claim 1 further comprising determining said $V_T$ data from RC data reflecting the size of said subject's ribcage and AB data reflecting the size of said subject's abdomen.

3. The method of claim 2 wherein a breath is also recognized as a respiratory event if a peak-to-peak amplitude of a breath in said $V_T$ data is not greater that a threshold but a peak-to-peak amplitude of that breath in corresponding AB data is greater than a threshold.

4. The method of claim 1 wherein said breath threshold is approximately 200 ml.

5. The method of claim 1 wherein said breath threshold is determined in dependence on breath volumes measured for said subject.

6. The method of claim 1 wherein said sound data is obtained from a sensor in contact with, or in close proximity to, said subject's throat.

7. The method of claim 1 wherein said sound envelope threshold is a selected multiple of calibrated background noise.

8. The method of claim 1
wherein if a duration of said overlapping sound event exceeds 600 msec., then low pass filtered $V_T$ data is processed in order to determine whether said respiratory event has said characteristic expiration-inspiration pattern; and
wherein if a duration of said overlapping sound event exceeds 600 msec., then high pass filtered $V_T$ data is processed in order to determine whether said respiratory event has said characteristic expiration-inspiration pattern.

9. The method of claim 1 wherein a respiratory event is determined to have said characteristic expiration-inspiration pattern if the period of expiration and the following period of inspiration of said respiratory event are symmetrically placed during said overlapping sound event so that a $V_T$ minimum of said respiratory event occurs in a central portion of said sound event.

10. The method of claim 1 wherein a respiratory event is determined to have said characteristic expiration-inspiration pattern if peak expiratory flow is greater than a threshold.

11. The method of claim 10 wherein said peak expiratory flow threshold is determined in dependence on peak expiratory flows measured for said subject.

12. The method of claim 1 further comprising, for each cough event,
determining a measure of pitch of said overlapping sound event;
retaining said selected cough event if said determined pitch measure indicates that said overlapping sound event does not include speech sounds; and otherwise
discarding said cough event if said determined pitch measure does not indicate that said overlapping sound event does not include speech sounds.

13. The method of claim 12 wherein said determining pitch comprises mel frequency wrapping.

14. The method of claim 12 wherein said pitch measure indicates that said overlapping sound event does not include speech sounds if a maximum pitch is less than a cough-speech threshold.

15. The method of claim 12 wherein said cough-speech threshold comprises a mel-frequency threshold of approximately 1.5 or greater.

16. The method of claim 12 wherein said pitch measure indicates that said overlapping sound event does not include speech sounds if the signal power at pitches below a cough-speech threshold increases.

17. The method of claim 12 wherein said pitch measure indicates that said overlapping sound event does not include speech sounds if the average of the recent maximum pitches is less than a cough-speech threshold.

18. The method of claim 1 further comprising, for each cough event,
processing accelerometer data obtained from said subject in order to recognize motion and/or change of posture of said subject;
retaining said selected cough event if no subject motion and/or change of posture is recognized during said cough and otherwise
discarding said cough event if subject motion and/or change of posture is recognized during said cough.

19. A computer-implemented method for monitoring a subject during sleep comprising:
monitoring data comprising tidal volume data, sound data, and EEG data with a monitoring device responsive to said subject;
processing said monitored respiratory data and sound data in order to recognize cough events;
processing said monitored EEG data in order to recognize transient arousal events; and
detecting a cough-arousal (CA) event when a recognized cough event occurs in association with a recognized EEG arousal event.

20. The method of claim 19 wherein said processing respiratory and sound data further comprises recognizing a breath as a cough event if said breath has a peak-to-peak amplitude that exceeds a threshold and also has an expiration-inspiration pattern characteristic of a cough, and if sound data has an envelope that exceed a threshold temporally overlaps said breath.

21. The method of claim 19 further comprising, for each cough event,
processing accelerometer data obtained from said subject in order to recognize motion of said subject;
retaining said selected cough event if no subject motion and/or change of posture is recognized during said cough; and otherwise
discarding said cough event if subject motion and/or change of posture is recognized during said cough.

22. The method of claim 19 wherein said processing EEG data further comprises:
filtering said EEG data in order to produce an EEG spectrogram reflecting the signal present in a plurality of selected frequency bands during a plurality of time intervals; and
recognizing an arousal event when said EEG spectrogram indicates an increase in signal above approximately 16 Hz for approximately 3 or more seconds and without spindle waveforms.

23. The method of claim 22 wherein an arousal is recognized only if it follows any prior recognized arousal by approximately 10 or more sec. of sleep.

24. The method of claim 22 wherein, during a period of REM sleep, an arousal is recognized only if said EEG signal changes are accompanied by an increase in the amplitude of a concurrent electrooculogram (EOG) signal.

25. The method of claim 19 wherein a cough event occurs in association with an arousal event when said sough event occurs within a predetermined time window that includes said arousal event.

26. The method of claim 25 wherein said predetermined time window comprises a 30 sec. time window.

27. The method of claim 19 further comprising determining a CA index (CAI) for a selected period of time as the number of CA events during said selected period of time.

28. The method of claim 27 further comprising determining a plurality of CAIs for selected periods of time spanning a period of sleep of said subject.

29. A computer-implemented method for monitoring cough in a subject comprising:
    monitoring data comprising tidal volume data, sound data, and EEG data with a monitoring device responsive to said subject;
    processing said monitored tidal volume ($V_T$) data in order to recognize a respiratory event when a breath has a peak-to-peak amplitude that exceeds a threshold and has an expiration-inspiration pattern characteristic of a cough;
    processing said monitored sound data in order to recognize a sound event when a sound envelope exceeds a threshold;
    recognizing a respiratory event as a cough event if said respiratory event temporally overlaps a sound event; and
    processing each cough event to determine a ratio of the depth of said cough event to a mean expiratory volume during a period of quiet breathing.

30. The method of claim 29 comprising further processing said $V_T$ data obtained from said subject during a period of quiet breathing in order to determine said mean expiratory volume.

31. The method of claim 29 further comprising classifying a recognized cough event in dependence on said determined ratio.

32. The method of claim 31 wherein a cough event is classified as a cough of cystic fibrosis if said ratio is in a range determined to be characteristic of cystic fibrosis coughs.

33. The method of claim 31 wherein a cough event is classified as a post-infectious cough if said ratio is in a range determined to be characteristic of post-infectious coughs, said post-infectious range being less than said cystic fibrosis range.

34. The method of claim 31 wherein a cough event is classified as a cough of chronic obstructive pulmonary disease (COPD) if said ratio is in a range determined to be characteristic of COPD coughs, said COPD range being less than said post-infectious range.

35. A system for monitoring a subject during sleep comprising:
    a monitoring garment comprising sensors providing respiratory signals, sound signals, and EEG signals from said subject; and
    a computer system comprising a computer-readable memory comprising encoded instructions for
        receiving said sensor signals;
        processing said respiratory signals and said sound signals in order to recognize cough events;
        processing said EEG signals in order to recognize transient arousal events;
        detecting a cough-arousal (CA) event when a recognized cough event occurs in association with a recognized EEG arousal event; and
        determining a CA index (CAI) for a plurality of selected time periods as the number of CA events during said selected period of time.

36. The system of claim 35 wherein said monitoring garment further comprises sensors providing accelerometer signals from said subject; and wherein said computer system further
    processes said accelerometer signals in order to recognize motion and/or change of posture of said subject;
    retains said selected cough event if no subject motion and/or change of posture is recognized during said cough; and otherwise
    discards said cough event if subject motion is recognized and/or change of posture during said cough.

37. The method of claim 35 wherein said sensor providing sound signals is in contact with, or in close proximity to, said subject's throat.

38. The system of claim 35 wherein said sensors comprise one or more sensors based in inductive plethysmographic (IP) technologies.

39. The system of claim 38 wherein said IP sensors comprise one or more of a sensor reflecting a size of said subject's rib cage and a sensor reflecting a size of said subject's abdomen.

40. The system of claim 35 wherein said monitoring garment comprises one or more of a band encircling a portion of said subject, a vest, a shirt, and a body suit.

41. A method of treating cough in a subject comprising:
    determining cough disturbance indices (CDI) for said subject for selected periods of time as the number of cough events during said selected periods of time, said cough events being determined by the method of claim 1;
    administering an anti-tussive therapeutic agent to said subject in order that said CDIs are within selected bounds.

42. A method of treating disordered sleep in a subject due to cough during sleep comprising:
    determining cough arousal indices (CAI) for selected periods when the subject is sleeping as the number of cough arousal events during said selected periods of time during sleep, said cough arousal events being determined by the method of claim 1; and
    administering an anti-tussive therapeutic agent to said subject in order that said CAIs are within selected bounds.

43. A method of evaluating a therapeutic agent in a subject comprising:
    determining a prior cough disturbance indices (CDI) for said subject for selected periods of time as the number of cough events during said selected periods of time, said cough events being determined by the method of claim 1;
    administering said therapeutic agent to said subject;
    determining subsequent CDIs for said subject for further selected periods of time; and
    comparing said prior CDIs with said subsequent CDIs to determine an effect of said therapeutic agent on cough of said subject.

44. A method for monitoring a subject during sleep comprising:
    Monitoring data comprising tidal volume data, sound data, and EEG data with a monitoring device responsive to said subject; and
    Transmitting said monitored data to a computer for
        Processing said respiratory signals and said sound signals in order to recognize cough events;
        Processing said EEG signals in order to recognize transient arousal events;

Detecting a cough-arousal (CA) event when a recognized cough event occurs in association with a recognized EEG arousal event; and Determining a CA index (CAI) for a plurality of selected time periods as the number of CA events during said selected period of time.

45. A method for monitoring cough in a subject, comprising:

Monitoring data comprising tidal volume data and sound data with a monitoring device responsive to said subject; and Transmitting said monitored data to a computer for Processing said volume ($V_T$) data in order to recognize a respiratory event when a peak-to-peak amplitude of a breath exceeds a threshold;

Processing said sound data in order to recognize a sound event when a sound envelope exceeds a threshold;

Processing each recognized respiratory event to determine if it temporally overlaps a sound event and further to determine if it has an expiration-inspiration pattern characteristic of a cough; and Selecting as a cough event each respiratory event that overlaps a sound event and has said characteristic expiration-inspiration pattern.

\* \* \* \* \*

UNITED STATES PATENT AND TRADEMARK OFFICE
CERTIFICATE OF CORRECTION

PATENT NO. : 7,207,948 B2 Page 1 of 1
APPLICATION NO. : 11/165956
DATED : April 24, 2007
INVENTOR(S) : Coyle It is certified that error appears in the above-identified patent and that said Letters Patent is hereby corrected as shown below:

Column 22:
Line 62 (claim 25, line 2), after "in association with an arousal event when said," delete "sough" and insert -- cough --.

Signed and Sealed this

Thirty-first Day of July, 2007

JON W. DUDAS
*Director of the United States Patent and Trademark Office*